(12) United States Patent
Lequeux et al.

(10) Patent No.: US 10,233,291 B2
(45) Date of Patent: Mar. 19, 2019

(54) ENHANCED AFFINITY LIGANDS

(71) Applicants: Nicolas Lequeux, Massy (FR); Thomas Pons, Paris (FR); Emerson Giovanelli, Laxou (FR)

(72) Inventors: Nicolas Lequeux, Massy (FR); Thomas Pons, Paris (FR); Emerson Giovanelli, Laxou (FR)

(73) Assignees: NEXDOT, Romainville (FR); FONDS DE L'ESPCI-GEORGES CHARPAK, Paris (FR)

( * ) Notice: Subject to any disclaimer, the term of this patent is extended or adjusted under 35 U.S.C. 154(b) by 194 days.

(21) Appl. No.: 14/406,306

(22) PCT Filed: Jun. 7, 2013

(86) PCT No.: PCT/EP2013/061863
§ 371 (c)(1),
(2) Date: Dec. 8, 2014

(87) PCT Pub. No.: WO2013/182707
PCT Pub. Date: Dec. 12, 2013

(65) Prior Publication Data
US 2015/0183939 A1 Jul. 2, 2015

Related U.S. Application Data

(60) Provisional application No. 61/656,699, filed on Jun. 7, 2012.

(30) Foreign Application Priority Data

Sep. 13, 2012 (EP) .................................. 12184331

(51) Int. Cl.
| | | |
|---|---|---|
| C08G 81/02 | (2006.01) | |
| A61K 49/00 | (2006.01) | |
| B82Y 15/00 | (2011.01) | |
| G01N 33/58 | (2006.01) | |
| C09K 11/56 | (2006.01) | |
| C09K 11/88 | (2006.01) | |
| C08F 8/04 | (2006.01) | |
| C08F 8/42 | (2006.01) | |
| H01B 1/12 | (2006.01) | |
| C08F 8/00 | (2006.01) | |
| A61K 47/54 | (2017.01) | |
| A61K 47/56 | (2017.01) | |
| A61K 47/58 | (2017.01) | |
| C08F 220/38 | (2006.01) | |
| C08F 220/60 | (2006.01) | |

(52) U.S. Cl.
CPC ........ C08G 81/025 (2013.01); A61K 49/0054 (2013.01); A61K 49/0067 (2013.01); B82Y 15/00 (2013.01); C08F 8/00 (2013.01); C08F 8/04 (2013.01); C08F 8/42 (2013.01); C09K 11/565 (2013.01); C09K 11/883 (2013.01); G01N 33/588 (2013.01); H01B 1/12 (2013.01); A61K 47/547 (2017.08); A61K 47/56 (2017.08); A61K 47/58 (2017.08); C08F 2220/387 (2013.01); C08F 2220/603 (2013.01); C08F 2220/606 (2013.01)

(58) Field of Classification Search
None
See application file for complete search history.

(56) References Cited

U.S. PATENT DOCUMENTS

| | | | |
|---|---|---|---|
| 7,432,326 B2 * | 10/2008 | Husemann | ............... A61B 6/00 348/E5.028 |
| 8,642,309 B2 | 2/2014 | Pucci et al. | |
| 2008/0139746 A1 * | 6/2008 | Pacetti | .................... A61L 27/34 525/188 |
| 2011/0037029 A1 | 2/2011 | Liu et al. | |
| 2011/0236315 A1 | 9/2011 | Han et al. | |
| 2013/0005016 A1 | 1/2013 | Pucci et al. | |
| 2014/0051883 A1 * | 2/2014 | Kim | ....................... B82B 1/005 562/106 |

FOREIGN PATENT DOCUMENTS

| | | | | |
|---|---|---|---|---|
| WO | WO-2011050070 A1 * | 4/2011 | ....... | G01N 33/54313 |
| WO | 2011-058195 | 5/2011 | | |

OTHER PUBLICATIONS

Dubertret et al., "In vivo imaging of quantum dots encapsulated in phospholipid micelles", pp. 1759-1762, vol. 298, 2002, Science.
Chan et al., "Quantum dot bioconjugates for ultrasensitive nonisotopic detection", pp. 2016-2028, vol. 281, 1998, Science.
Matoussi et al., "Self-Assembly of CdSe—ZnS Quantum Dot Bioconjugates Using an Engineered Recombinant Protein", pp. 12142-12150, vol. 1222, 2000, Journal of American Chemical Society.
Muro et al., "Small and stable sulfobetaine zwitterionic quantum dots for functional live-cell imaging", pp. 4556-4557, vol. 132, 2010, Journal of American Chemical Society.
Norton et al., "In vitro characterization of vascular endothelial growth factor and dexamethasone releasing hydrogels for implantable proble coatings", pp. 3285-3297, vol. 26, No. 16, 2004, Biomaterials.
Justin et al., "Electroconductive Blends of Poly(HEMA-co-PEGMA-co-HMMAco-SPMA) and Poly(Py-co-PyBA):In vitro biocompatibility", pp. 121-140, vol. 25, 2009, Journal of Bioactive and Compatible Polymers.
European Search Report, dated Jun. 27, 2013, from corresponding EP application No. EP 12184331.
International Search Report, dated Jul. 4, 2013, from corresponding PCT application No. PCT/EP2013/061863.
Michalet et al. "Quantum Dots for Live Cells, In vivo imaging and diagnostics" pp. 538, vol. 307, 2005, Science.
Medintz et al. "Quantum dot bioconjugates for imaging, labelling and sensing" pp. 435, vol. 4, 2005, Nat. Mater.
Brichkin et al., "Hydrophilic semiconductor quantum dots", pp. 1-12, vol. 45, N. 1, 2011, High Energy Chem.

(Continued)

Primary Examiner — James W Rogers
(74) Attorney, Agent, or Firm — Young & Thompson

(57) ABSTRACT

The present invention relates to ligands, nanocrystal complexed with the ligands and their use for bio-imaging.

6 Claims, 9 Drawing Sheets

(56) References Cited

OTHER PUBLICATIONS

Liu et al. "Compact cysteine-coated CdSe(ZnCdS) quantum dots for in vivo applications", pp. 14530-14531, vol. 129, 2007, J. Am. Chem. Soc.

Mei et al. "Effects of ligand coordination number and surface curvature on the stability of gold nanoparticles in aqueous solutions", pp. 10604-10611, vol. 25, 2009, Langmuir.

Liu et al. "Bifunctional Multidentate Ligand Modified Highly Stable Water-Soluble Quantum Dots", pp. 3768-3775, vol. 49, 2010, Inorg. Chem.

Yildiz et al. "Hydrophilic CdSe-ZnS core-shell quantum dots with reactive functional groups on their surface", pp. 11503-11511, vol. 26, 2010, Langmuir.

Stewart et al. "Multidentate poly(ethylene glycol) ligands provide colloidal stability to semiconductor and metallic nanocrystals in extreme conditions", pp. 9804-9813, vol. 132, 2010, Am. Chem. Soc.

Palui et al. "Poly(ethylene glycol)-based multidentate oligomers for biocompatible semiconductor and gold nanocrystals", pp. 2761-2772, vol. 28, 2012, Langmuir.

Ellman, G. L. "Tissue sulfhydryl groups" Arch. Biochem. Biophys. 1959, vol. 82, pp. 70-77.

Riddles et al. "Ellman's reagent: 5,5'-dithiobis(2-nitrobenzoic acid)—a reexamination", pp. 75-81, vol. 94, 1979, Anal. Biochem.

Pong et al. "Modified ligand-exchange for efficient solubilization of CdSe/ZnS quantum dots in water: a procedure guided by computational studies.", pp. 5270-5276, vol. 24, 2008, Langmuir.

Mary et al. "Reconciling Low- and High-Salt Solution Behavior of Sulfobetaine Polyzwitterions", pp. 7767-7767, vol. 111, 2007, Phys. Chem. B.

Muro et al. "Comparing intracellular stability and targeting of sulfobetaine quantum dots with other surface chemistries in live cells.", pp. 1029, vol. 8, 2012, Small.

Wilson et al. "Highly Stable Dextran-Coated Quantum Dots for Biomolecular Detection and Cellular Imaging", pp. 6361-6369, vol. 22, 2010, Chem. Mater.

* cited by examiner $$-\frac{d[\text{L2-fluorescein}]_{QDs}}{dt} = \frac{d[\text{L2-fluorescein}]_{solution}}{dt}$$

$$= k_{off\,L2\text{-fluorescein}} \cdot [\text{L2-fluorescein}]_{QDs}$$

$$\Rightarrow \quad [\text{L2-fluorescein}]_{QDs,t} = \exp(-k_{off\,L2\text{-fluorescein}} \cdot t) [\text{L2-fluorescein}]_{QDs,t=0}$$

ENHANCED AFFINITY LIGANDS

FIELD OF INVENTION

The present invention relates to ligands, nanocrystals complexed with said ligands and their use for bio-imaging.

BACKGROUND OF INVENTION

Colloidal semiconductor nanoparticles, named "quantum dots" (QDs), are crystalline objects that exhibit specific fluorescence properties. Their absorption cross section is very large, they are bright and their emission spectra have a small full width half maximum, and a peak wavelength that is tunable as a function of their composition, their size and their shape (in the range of a few nanometers to few tens of nanometers). They are also far more resistant to photobleaching than traditional organic dyes. These unique features make them very attractive for diverse applications in the field of medical and biological imaging, such as individual proteins monitoring, multi-color immunostaining, stem cells tracking, fluorescence acquisition cell sorting, or optically assisted surgery.

However, typical QD syntheses provide colloidal solutions of fluorescent nanocrystals capped with hydrophobic ligands, while the use of QDs in live-cell imaging requires their complete solubility in water as well as an excellent compatibility with biological media. To make the QDs water-soluble, two major methods exist: either the encapsulation of as-synthesized QDs with amphiphilic molecules into micelle-like structures (Dubertret et al. Science 2002, 298:1759), or a cap exchange, consisting in the replacement of original ligands by hydrophilic ones, bearing a chemical function able to bind to the nanocrystal surface (Chan et al. Science 1998, 281:2016 and Mattoussi et al. J. Am. Chem. Soc. 2000, 122:12142). Encapsulation is a very mild method, leading to the brighter nanoparticles, whereas cap exchange results in much smaller and more stable QDs. For both techniques, the non-specific interactions of the QD with cell membranes or with biomolecules in general depend mainly on the moieties that are adsorbed on the QD surface. In comparison to encapsulation, ligand exchange provides a versatile method to control the size, the nature of the ligand as well as its affinity for the QD surface (ligands that are too strong can indeed dissolve the QD, while ligands that are not strong enough can detach from the QD surface). This versatility explains why cap exchange is by far the most common technique to make the QDs water-soluble.

Ligand desorption is a strong limitation for the use of QDs in bio-imaging. This desorption, favored in high diluted conditions, causes indeed a loss of colloidal stability and functionality, as well as an increase in aggregation and non-specific adsorption. As a consequence, continued efforts have been made to improve the affinity of passivating ligands for the QD surface. The design of these replacing ligands is also guided by further needs for biological applications of quantum dots, namely: small size; stability over a large pH range, at elevated salt concentrations and in a cellular medium; low non-specific adsorption; and possible functionalization afterwards.

To match the above-mentioned criteria, the inventors first developed a zwitterionic ligand L1 connecting a dithiol, as bidentate linking function, to a sulfobetaine part, as aqueous solubility promoter (Scheme 1) (Muro et al. J. Am. Chem. Soc. 2010, 132:4556).

Scheme 1. Chemical structure of ligand L1.

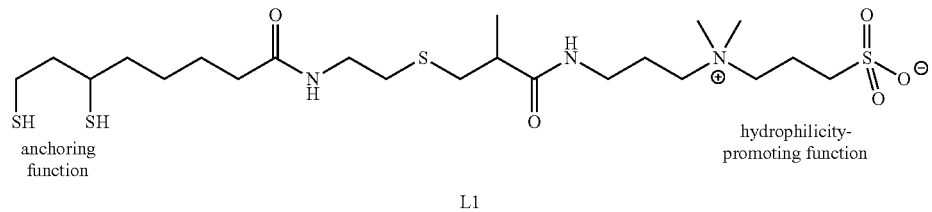

L1

However QDs coated with this ligand L1 suffered from a lack of colloidal stability, mainly at high nanoparticle dilutions, due to ligand desorption.

There is thus a need for new ligands that exhibit high affinity for the QD surface (implying QD high colloidal stability), as well as a small size; a low non-specific adsorption; and possible functionalization afterwards.

SUMMARY

One object of the invention is a ligand which is a copolymer comprising at least 2 monomers and having the following formula I:

$(A)_x(B)_y$, wherein

A comprises at least one anchoring monomer comprising a first moiety $M_A$ having affinity for the surface of a nanocrystal, B comprises at least one hydrophilic monomer comprising a second moiety $M_B$ having a high water solubility, and each of x and y is independently a positive integer, wherein when B comprises a monomer comprising a second moiety $M_B$ which is a PEG moiety, then B further comprises at least one monomer comprising a second moiety $M_B$ which is not a PEG moiety.

In one embodiment, x+y is ranging from 5 to 500.

In another embodiment, said ligand has the following formula II':

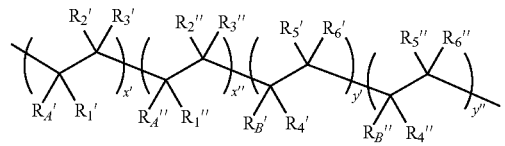

wherein $R_A'$ and $R_A''$ represent respectively a group comprising a first moiety $M_A$ having affinity for the surface of a nanocrystal, respectively $M_A'$ and $M_A''$, $R_B'$ and $R_B''$ represent respectively a group comprising a second moiety $M_B$ having a high water solubility, respectively $M_B'$ and $M_B''$, $R_1'$, $R_2'$, $R_3'$, $R_1''$, $R_2''$, $R_3''$, $R_4'$, $R_5'$, $R_6'$, $R_4''$, $R_5''$, $R_6''$ can be independently H, or a group selected from an alkyl, alkenyl, aryl, hydroxyle, halogen, alkoxy, carboxylate, C comprises at least one functionalizable monomer comprising a third moiety $M_C$ having a reactive function, and each of x, y and z is independently a positive integer, preferably x+y+z is ranging from 5 to 750.

In another embodiment, said ligand has the following formula IV':

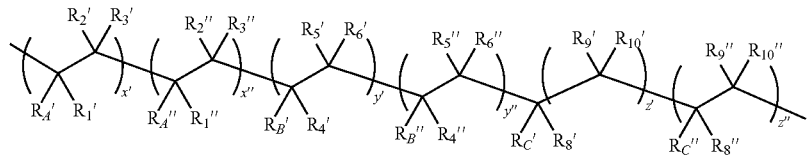

each of x' and x" is independently a positive integer, preferably an integer ranging from 0 to 499, with the condition that at least one of x' and x" is not 0, each of y' and y" is independently a positive integer, preferably an integer ranging from 0 to 499, with the condition that at least one of y' and y" is not 0.

In another embodiment, said first moiety $M_A$, $M_A'$ or $M_A''$ having affinity for the surface of a nanocrystal is a thiol moiety, a dithiol moiety, an imidazole moiety, a catechol moiety, a pyridine moiety, a pyrrole moiety, a thiophene moiety, a thiazole moiety, a pyrazine moiety, a carboxylic acid or carboxylate moiety, a naphthyridine moiety, a phosphine moiety, a phosphine oxide moiety, a phenol moiety, a primary amine moiety, a secondary amine moiety, a tertiary amine moiety, a quaternary amine moiety, an aromatic amine moiety, or a combination thereof.

In another embodiment, said second moiety $M_B$, $M_B'$ or $M_B''$ having a high water solubility is a zwitterionic moiety such as for example an aminocarboxylate, an aminosulfonate, a carboxybetaine moiety wherein the ammonium group may be included in an aliphatic chain, a five-membered cycle, a five-membered heterocycle comprising 1, 2 or 3 further nitrogen atoms, a six-membered cycle, a six-membered heterocycle comprising 1, 2, 3 or 4 further nitrogen atoms, a sulfobetaine moiety wherein the ammonium group may be included in an aliphatic chain, a five-membered cycle, a five-membered heterocycle comprising 1, 2 or 3 further nitrogen atoms, a six-membered cycle, a six-membered heterocycle comprising 1, 2, 3 or 4 further nitrogen atoms, a phosphobetaine wherein the ammonium group may be included in an aliphatic chain, a five-membered cycle, a five-membered heterocycle comprising 1, 2 or 3 further nitrogen atoms, a six-membered cycle, a six-membered heterocycle comprising 1, 2, 3 or 4 further nitrogen atoms, a phosphorylcholine, a phosphocholine moiety, and combinations thereof or a PEG moiety.

In another embodiment, said first moiety $M_A$, $M_A'$ or $M_A''$ having affinity for the surface of a nanocrystal is dithiol moiety, preferably a propane-1,3-dithiol, more preferably a propan-1-yl-1,3-dithiol moiety.

In another embodiment, said second moiety $M_B$, $M_B'$ or $M_B''$ having a high water solubility is a sulfobetaine group.

In another embodiment, said ligand has the following formula III:

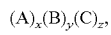

wherein
A is as defined in claim 1,
B is as defined in claim 1, wherein
$R_A'$, $R_A''$, $R_B'$, $R_B''$, $R_1'$, $R_2'$, $R_3'$, $R_1''$, $R_2''$, $R_3''$, $R_4'$, $R_5'$, $R_6'$, $R_4''$, $R_5''$, and $R_6''$ are defined here above, $R_C'$ and $R_C''$ represent respectively a group comprising a third moiety $M_C$, respectively $M_C'$ and $M_C''$, and $R_8'$, $R_9'$, $R_{10}'$, $R_8''$, $R_9''$, and $R_{10}''$ can be independently H, or a group selected from an alkyl, alkenyl, aryl, hydroxyl, halogen, alcoxy, carboxylate, each of x' and x" is independently a positive integer, preferably an integer ranging from 0 to 499, with the condition that at least one of x' and x" is not 0, each of y' and y" is independently a positive integer, preferably an integer ranging from 0 to 499, with the condition that at least one of y' and y" is not 0, each of z' and z" is independently a positive integer, preferably an integer ranging from 0 to 499, with the condition that at least one of z' and z" is not 0.

In another embodiment, said third moiety $M_C$, $M_C'$ or $M_C''$ is any moiety having an amine group such as a primary amine group, any moiety having an azido group, any moiety having an alkenyl group, any moiety having an acidic function, any moiety having an alcoholic group, any moiety having a thiol group, any moiety that can form a non covalent bond with a selective binding counterpart, said moiety being for example biotin, a nucleic acid, FK506, or an antibody.

Another object of the invention is a ligand as defined here above, being functionalized with at least one molecular probe and/or targeting group.

Another object of the invention is a nanocrystal being complexed with at least one ligand as defined here above.

In one embodiment, said nanocrystal is a quantum dot, a nanoplatelet or a quantum dot having its lateral dimensions larger than its thickness.

In one embodiment, said nanocrystal is a 0D, 1D, or 2D nanocrystal, preferably a nanosheet, a nanorod, a nanoplatelet, a nanoplate, a nanoprism, a nanowall, a nanodisk, a nanoparticle, a nanowire, a nanopowder, a nanotube, a nanotetrapod, a nanoribbon, a nanobelt, a nanoneedle, a nanocube, a nanoball, a nanocoil, a nanocone, a nanopiller, a nanoflower, or a quantum dot.

Another object of the invention is a water-soluble composition comprising at least one nanocrystal being complexed with at least one ligand as defined here above.

Another object of the invention is the use of said nanocrystal being complexed with at least one ligand as defined here above or said water-soluble composition as defined here above for bioimaging, biotargeting, medical imaging or biosensing.

DEFINITIONS

In the present invention, the following terms have the following meanings:

"alkyl" refers to any saturated linear or branched hydrocarbon chain, with 1 to 12 carbon atoms, preferably 1 to 6 carbon atoms, and more preferably methyl, ethyl, propyl, isopropyl, n-butyl, sec-butyl, isobutyl and tert-butyl. The alkyl group may be substituted by a saturated or unsaturated aryl group.

When the suffix "ene" ("alkylene") is used in conjunction with an alkyl group, this is intended to mean the alkyl group as defined herein having two single bonds as points of attachment to other groups. The term "alkylene" includes methylene, ethylene, methylmethylene, propylene, ethylethylene, and 1,2-dimethylethylene.

"alkenyl" refers to any linear or branched hydrocarbon chain having at least one double bond, of 2 to 12 carbon atoms, and preferably 2 to 6 carbon atoms. The alkenyl group may be substituted. Examples of alkenyl groups are ethenyl, 2-propenyl, 2-butenyl, 3-butenyl, 2-pentenyl and its isomers, 2-hexenyl and its isomers, 2,4-pentadienyl and the like. The alkenyl group may be substituted by a saturated or unsaturated aryl group.

"alkynyl", refers to any linear or branched hydrocarbon chain having at least one triple bond, of 2 to 12 carbon atoms, and preferably 2 to 6 carbon atoms.

The terms "alkenylene" means an alkenyl group as defined above having two single bonds as points of attachment to other groups.

"aryl" refers to a mono- or polycyclic system of 5 to 20, and preferably 6 to 12, carbon atoms having one or more aromatic rings (when there are two rings, it is called a biaryl) among which it is possible to cite the phenyl group, the biphenyl group, the 1-naphthyl group, the 2-naphthyl group, the tetrahydronaphthyl group, the indanyl group and the binaphthyl group. The term aryl also means any aromatic ring including at least one heteroatom chosen from an oxygen, nitrogen or sulfur atom. The aryl group can be substituted by 1 to 3 substituents chosen independently of one another, among a hydroxyl group, a linear or branched alkyl group comprising 1, 2, 3, 4, 5 or 6 carbon atoms, in particular methyl, ethyl, propyl, butyl, an alkoxy group or a halogen atom, in particular bromine, chlorine and iodine, a nitro group, a cyano group, an azido group, an adhehyde group, a boronato group, a phenyl, $CF_3$, methylenedioxy, ethylenedioxy, $SO_2NRR'$, NRR', COOR (where R and R' are each independently selected from the group consisting of H and alkyl), an second aryl group which may be substituted as above. Non-limiting examples of aryl comprise phenyl, biphenylyl, biphenylenyl, 5- or 6-tetralinyl, naphthalen-1- or -2-yl, 4-, 5-, 6 or 7-indenyl, 1- 2-, 3-, 4- or 5-acenaphtylenyl, 3-, 4- or 5-acenaphtenyl, 1- or 2-pentalenyl, 4- or 5-indanyl, 5-, 6-, 7- or 8-tetrahydronaphtyl, 1,2,3,4-tetrahydronaphtyl, 1,4-dihydronaphtyl, 1-, 2-, 3-, 4- or 5-pyrenyl.

The term "arylene" as used herein is intended to include divalent carbocyclic aromatic ring systems such as phenylene, biphenylylene, naphthylene, indenylene, pentalenylene, azulenylene and the like.

"cycle" refers to a saturated, partially unsaturated or unsaturated cyclic group.

"heterocycle" refers to a saturated, partially unsaturated or unsaturated cyclic group comprising at least on heteroatom.

"halogen" means fluoro, chloro, bromo, or iodo. Preferred halo groups are fluoro and chloro.

"alkoxy" refers to any O-alkyl group, preferably an O-alkyl group wherein the alkyl group has 1 to 6 carbon atoms.

"aryloxy" refers to any O-aryl group.

"arylalkyl" refers to an alkyl group substituted by an aryl group, such as for example the phenyl-methyl group.

"arylalkoxy" refers to an alkoxy group substituted by an aryl group.

"amine" refers to any group derived from ammoniac $NH_3$ by substitution of one or more hydrogen atoms with an organic radical.

"azido" refers to $—N_3$ group.

"acidic function" refers to —COOH group.

"activated acidic function" refers to an acidic function wherein the —OH is replaced by a better leaving group.

"activated alcoholic function" refers to an alcoholic function modified to be a better leaving group.

DETAILED DESCRIPTION

One object of the invention is a ligand which is a copolymer comprising at least 2 monomers, said monomers being:
one anchoring monomer comprising a first moiety $M_A$ having affinity for the surface of a nanocrystal, and
one hydrophilic monomer comprising a second moiety $M_B$ having a high water solubility.

In one embodiment, the first moiety $M_A$ having affinity for the surface of a nanocrystal has preferably affinity for a metal present at the surface of a nanocrystal or for a material E present at the surface of a nanocrystal and selected in the group of O, S, Se, Te, N, P, As, and mixture thereof.

Examples of metal present at the surface of a nanocrystal include, but are not limited to, gold, iron oxide, titanium dioxide, cerium oxide, metal chalcogenide, metal pnictide, cadmium, zinc, magnesium, mercury, aluminium, gallium, indium, thallium, copper, cobalt, platinum, silver, tin, lead and mixtures thereof.

In one embodiment of the invention, said ligand is a copolymer having a plurality of monomers including the monomer A and the monomer B. In one embodiment, said ligand is a random or block copolymer. In another embodiment, said ligand is a random or block copolymer consisting essentially of monomer A and monomer B. In one embodiment of the invention, said ligand is a multi-dentate ligand.

In one embodiment of the invention, said ligand has the following formula I:

wherein

A comprising at least one anchoring monomer comprising a first moiety $M_A$ having affinity for the surface of a nanocrystal as described here above, B comprising at least one hydrophilic monomer comprising a second moiety $M_B$ having a high water solubility, and each of x and y is independently a positive integer, preferably an integer ranging from 1 to 499, from 1 to 249, from 1 to 99, or from 1 to 24.

In one embodiment, each of x and y is independently a positive integer, preferably an integer selected in the group of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30.

In one embodiment of the invention, x+y is ranging from 5 to 500, from 5 to 250, from 5 to 100, from 5 to 75, from 5 to 50, from 10 to 50, from 10 to 30, from 5 to 35, from 5 to 25, from 15 to 25.

In one embodiment, when B comprises a monomer comprising a second moiety $M_B$ which is a PEG moiety, then B further comprises at least one monomer comprising a second moiety $M_B$ which is not a PEG moiety.

In another embodiment of the invention, said ligand has the following formula II:

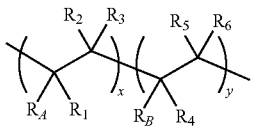

wherein $R_A$ represents a group comprising the first moiety $M_A$ having affinity for the surface of a nanocrystal as described here above, $R_B$ represents a group comprising the second moiety $M_B$ having a high water solubility, $R_1$, $R_2$, $R_3$, $R_4$, $R_5$, $R_6$ can be independently H, or a group selected from an alkyl, alkenyl, aryl, hydroxyle, halogen, alkoxy, carboxylate, each of x and y is independently a positive integer, preferably an integer ranging from 1 to 499.

In one embodiment, each of x and y is independently a positive integer, preferably an integer selected in the group of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30.

In one embodiment of the invention, x+y is ranging from 5 to 500, from 5 to 250, from 5 to 100, from 5 to 75, from 5 to 50, from 10 to 50, from 10 to 30, from 5 to 35, from 5 to 25, from 15 to 25.

In one embodiment of the invention, $R_2$, $R_3$, $R_5$ and $R_6$ are H.

In one embodiment of the invention, $R_1$ and $R_4$ are alkyl groups, preferably methyl.

In one embodiment of the invention, said first moiety $M_A$ having affinity for the surface of a nanocrystal and in particular affinity for a metal present at the surface of a nanocrystal includes, but is not limited to, a thiol moiety, a dithiol moiety, an imidazole moiety, a catechol moiety, a pyridine moiety, a pyrrole moiety, a thiophene moiety, a thiazole moiety, a pyrazine moiety, a carboxylic acid or carboxylate moiety, a naphthyridine moiety, a phosphine moiety, a phosphine oxide moiety, a phenol moiety, a primary amine moiety, a secondary amine moiety, a tertiary amine moiety, a quaternary amine moiety, an aromatic amine moiety, or a combination thereof.

In one embodiment of the invention, said first moiety $M_A$ having affinity for the surface of a nanocrystal and in particular affinity for a material E selected in the group of O, S, Se, Te, N, P, As, and mixture thereof, includes, but is not limited to, an imidazole moiety, a pyridine moiety, a pyrrole moiety, a thiazole moiety, a pyrazine moiety, a naphthyridine moiety, a phosphine moiety, a phosphine oxide moiety, a primary amine moiety, a secondary amine moiety, a tertiary amine moiety, a quaternary amine moiety, an aromatic amine moiety, or a combination thereof.

In one embodiment of the invention, said first moiety $M_A$ is not a dihydrolipoic acid (DHLA) moiety.

In another embodiment of the invention, said first moiety $M_A$ is not an imidazole moiety.

In one embodiment of the invention, said first moiety $M_A$ having affinity for the surface of a nanocrystal is a dithiol moiety, preferably a propane-1,3-dithiol, more preferably a propan-1-yl-1,3-dithiol moiety.

Thiol-based ligands complexed to QD were considered in the art as inherently unstable as the thiol group can undergo oxidation and dimerization, causing the ligand to detach from the QD surface over time. Surprisingly, the inventors show herein that a thiol-based ligand complexed to QD is unexpectedly stable over time (see Examples). Without willing to be bound to a theory, the inventors think that even if the thiol groups can undergo oxidation and dimerization, the multiple number of thiol groups present in the ligand of the invention may maintain the copolymer near the QD surface and favors their re-attachment to the QD surface.

In one embodiment of the invention, said second moiety $M_B$ having a high water solubility includes, but is not limited to, a zwitterionic moiety (i.e. any compound having both a negative charge and a positive charge, preferably a group with both an ammonium group and a sulfonate group or a group with both an ammonium group and a carboxylate group) such as for example an aminocarboxylate, an aminosulfonate, a carboxybetaine moiety wherein the ammonium group may be included in an aliphatic chain, a five-membered cycle, a five-membered heterocycle comprising 1, 2 or 3 further nitrogen atoms, a six-membered cycle, a six-membered heterocycle comprising 1, 2, 3 or 4 further nitrogen atoms, a sulfobetaine moiety wherein the ammonium group may be included in an aliphatic chain, a five-membered cycle, a five-membered heterocycle comprising 1, 2 or 3 further nitrogen atoms, a six-membered cycle, a six-membered heterocycle comprising 1, 2, 3 or 4 further nitrogen atoms, a phosphobetaine wherein the ammonium group may be included in an aliphatic chain, a five-membered cycle, a five-membered heterocycle comprising 1, 2 or 3 further nitrogen atoms, a six-membered cycle, a six-membered heterocycle comprising 1, 2, 3 or 4 further nitrogen atoms, a phosphorylcholine, a phosphocholine moiety, and combinations thereof or a PEG moiety.

In another embodiment of the invention, said second moiety $M_B$ having a high water solubility is not a PEG moiety.

An example of a suitable PEG moiety is —[O—CH$_2$—CHR']$_n$—R", wherein R' can be H or $C_1$-$C_3$ alkyl, R" can be H, —OH, $C_1$-$C_6$ alkyl, $C_1$-$C_6$ alkoxy, aryl, aryloxy, arylalkyl, or arylalkoxy and n can be an integer in the range of 1 to 120, preferably of 1 to 60, more preferably of 1 to 30.

In one embodiment of the invention, said second moiety $M_B$ having a high water solubility is a sulfobetaine group.

In one embodiment of the invention, when the first moiety $M_A$ is an imidazole moiety, the second moiety $M_B$ is not a PEG moiety.

In one embodiment of the invention, when the first moiety $M_A$ is an imidazole moiety, the second moiety $M_B$ is not a sulfobetaine moiety. In a specific embodiment of the invention, when the first moiety $M_A$ is an imidazole moiety, the second moiety $M_B$ is not —N$^+$(Me)$_2$(CH$_2$)$_2$—SO$_3^-$ or —N$^+$(Me)$_2$-(CH$_2$)$_3$—SO$_3^-$.

In one embodiment of the invention, when the first moiety $M_A$ is an imidazole moiety, the second moiety $M_B$ is not a carboxybetaine moiety. In a specific embodiment of the invention, when the first moiety $M_A$ is an imidazole moiety, the second moiety $M_B$ is not —N$^+$(Me)$_2$-(CH$_2$)$_2$—COO$^-$.

In one embodiment of the invention, when the first moiety $M_A$ is an imidazole moiety, the second moiety $M_B$ is not a phosphobetaine moiety. In a specific embodiment of the invention, when the first moiety $M_A$ is an imidazole moiety, the second moiety $M_B$ is not —O—P($O_2^-$)—P—($CH_2$)$_2$—$N^+$(Me)$_3$.

In one embodiment of the invention, when the first moiety $M_A$ is a dithiol group, and B comprises a monomer comprising a second moiety $M_B$' which is a PEG moiety, then B further comprises at least one monomer comprising a second moiety $M_B$" which is not a PEG moiety.

In another embodiment of the invention, said ligand has the following formula II':

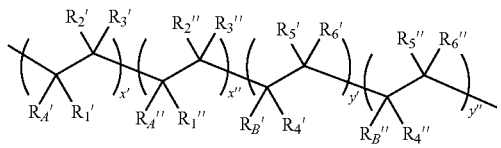

wherein $R_A$' and $R_A$" represent respectively a group comprising the first moiety $M_A$' and $M_A$" having affinity for the surface of a nanocrystal, $R_B$' and $R_B$" represent respectively a group comprising the second moiety $M_B$' and $M_B$" having a high water solubility, $R_1$', $R_2$', $R_3$', $R_1$", $R_2$", $R_3$", $R_4$', $R_5$', $R_6$', $R_4$", $R_5$", $R_6$" can be independently H, or a group selected from an alkyl, alkenyl, aryl, hydroxyle, halogen, alkoxy, carboxylate, each of x' and x" is independently a positive integer, preferably an integer ranging from 0 to 499, with the condition that at least one of x' and x" is not 0, each of y' and y" is independently a positive integer, preferably an integer ranging from 0 to 499, with the condition that at least one of y' and y" is not 0.

In one embodiment, each of x' and x" is independently a positive integer, preferably an integer selected in the group of 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, with the condition that at least one of x' and x" is not 0.

In one embodiment, each of y' and y" is independently a positive integer, preferably an integer selected in the group of 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, with the condition that at least one of y' and y" is not 0.

In one embodiment of the invention, x'+x"+y'+y" is ranging from 5 to 500, from 5 to 250, from 5 to 100, from 5 to 75, from 5 to 50, from 10 to 50, from 10 to 30, from 5 to 35, from 5 to 25, from 15 to 25.

In one embodiment of the invention, $R_2$', $R_3$', $R_2$", $R_3$", $R_5$', $R_6$', $R_5$" and $R_6$" are H.

In one embodiment of the invention, $R_1$', $R_1$", $R_4$' and $R_4$" are alkyl groups, preferably methyl.

In one embodiment of the invention, said moiety $M_A$ comprises said moieties $M_A$' and $M_A$".

In one embodiment of the invention, said moiety $M_B$ comprises said moieties $M_B$' and $M_B$".

In one embodiment of the invention, said x is equal to x'+x".

In one embodiment of the invention, said y is equal to y'+y".

In one embodiment of the invention, said first moieties $M_A$' and $M_A$" having affinity for the surface of a nanocrystal and in particular affinity for a metal present at the surface of a nanocrystal include, but is not limited to, a thiol moiety, a dithiol moiety, an imidazole moiety, a catechol moiety, a pyridine moiety, a pyrrole moiety, a thiophene moiety, a thiazole moiety, a pyrazine moiety, a carboxylic acid or carboxylate moiety, a naphthyridine moiety, a phosphine moiety, a phosphine oxide moiety, a phenol moiety, a primary amine moiety, a secondary amine moiety, a tertiary amine moiety, a quaternary amine moiety, an aromatic amine moiety, or a combination thereof.

In one embodiment of the invention, said first moieties $M_A$' and $M_A$" having affinity for the surface of a nanocrystal and in particular affinity for a material E selected in the group of O, S, Se, Te, N, P, As, and mixture thereof, include, but is not limited to, an imidazole moiety, a pyridine moiety, a pyrrole moiety, a thiazole moiety, a pyrazine moiety, a naphthyridine moiety, a phosphine moiety, a phosphine oxide moiety, a primary amine moiety, a secondary amine moiety, a tertiary amine moiety, a quaternary amine moiety, an aromatic amine moiety, or a combination thereof.

In one embodiment of the invention, said first moiety $M_A$' having affinity for the surface of a nanocrystal is a dithiol moiety and said first moiety $M_A$" having affinity for the surface of a nanocrystal is an imidazole moiety.

In one embodiment of the invention, said second moieties $M_B$' and $M_B$" having a high water solubility include, but is not limited to, a zwitterionic moiety (i.e. any compound having both a negative charge and a positive charge, preferably a group with both an ammonium group and a sulfonate group or a group with both an ammonium group and a carboxylate group) such as for example an aminocarboxylate, an aminosulfonate, a carboxybetaine moiety wherein the ammonium group may be included in an aliphatic chain, a five-membered cycle, a five-membered heterocycle comprising 1, 2 or 3 further nitrogen atoms, a six-membered cycle, a six-membered heterocycle comprising 1, 2, 3 or 4 further nitrogen atoms, a sulfobetaine moiety wherein the ammonium group may be included in an aliphatic chain, a five-membered cycle, a five-membered heterocycle comprising 1, 2 or 3 further nitrogen atoms, a six-membered cycle, a six-membered heterocycle comprising 1, 2, 3 or 4 further nitrogen atoms, a phosphobetaine wherein the ammonium group may be included in an aliphatic chain, a five-membered cycle, a five-membered heterocycle comprising 1, 2 or 3 further nitrogen atoms, a six-membered cycle, a six-membered heterocycle comprising 1, 2, 3 or 4 further nitrogen atoms, a phosphorylcholine, a phosphocholine moiety, and combinations thereof or a PEG moiety, wherein if $M_B$' is a PEG moiety, then $M_B$" is not a PEG moiety and inversely. In one embodiment of the invention, said second moiety $M_B$' having a high water solubility is a sulfobetaine group and said second moiety $M_B$" having a high water solubility is a PEG moiety.

In one embodiment of the invention, said ligand is a copolymer synthesized from at least 2 monomers, said monomers being:
  one anchoring monomer wherein $M_A$ is a dithiol group,
  one hydropohilic monomer wherein $M_B$ is a sulfobetaine group.

In one embodiment of the invention, $R_A$ comprising the first moiety $M_A$ can have the formula -$L_A$-$M_A$, wherein $L_A$ can be a bond or an alkylene, alkenylene, or arylene linking group having 1 to 8 chain atoms and can be optionally interrupted or terminated by —O—, —S—, —$NR_7$—, wherein $R_7$ is H or alkyl, —CO—, —NHCO—, —CONH— or a combination thereof and $M_A$ corresponds to the first moiety as described here above.

Preferably, $L_A$ is —C(=O)—NH—($CH_2$)$_m$—NH—C(=O)—($CH_2$)$_p$—, wherein m is an integer ranging from 1 to 5, preferably 2, 3, 4 and p is an integer ranging from 1 to 6, preferably 3, 4, 5.

In a preferred embodiment, -L$_A$-M$_A$ is

[chemical structure]

wherein m, p and M$_A$ are as defined above, preferably m is equal to 3 and p is equal to 4.

In a preferred embodiment, M$_A$ is a dithiol moiety and -L$_A$-M$_A$ may be represented by

[chemical structure]

wherein m, p and M$_A$ are as defined above, preferably m is equal to 3 and p is equal to 4.

In a preferred embodiment, -L$_A$-M$_A$ is

[chemical structure]

wherein m, p and M$_A$ are as defined above preferably m is equal to 3 and p is equal to 4.

In a preferred embodiment, -L$_A$-M$_A$ is

[chemical structure]

In one embodiment of the invention, R$_B$ comprising the second moiety M$_B$ can have the formula -L$_B$-M$_B$, wherein L$_B$ can be a bond or an alkylene, alkenylene, or arylene linking group having 1 to 8 chain atoms and can be optionally interrupted or terminated by —O—, —S—, —NR$_7$—, wherein R$_7$ is H or alkyl, —CO—, —NHCO—, —CONH— or a combination thereof and M$_B$ corresponds to the second moiety as described here above.

Preferably, L$_B$ is —C(=O)—NH—(CH$_2$)$_q$—, wherein q is an integer ranging from 1 to 5, preferably 2, 3, 4.

In a preferred embodiment, -L$_B$-M$_B$ is

[chemical structure]

wherein q and M$_B$ are as defined above, preferably q is equal to 3.

In a preferred embodiment, -L$_B$-M$_B$ may be represented by

[chemical structure]

wherein q is as defined above and M$_B$ is a zwitterionic moiety, preferably q is equal to 3.

In one preferred embodiment, -L$_B$-M$_B$ may be represented by

[chemical structure]

wherein q is as defined above, preferably q is equal to 3 s is an integer ranging from 1 to 5, preferably s is equal 2, 3 or 4,

R$_{12}$, R$_{13}$, R$_{14}$ and R$_{15}$ are each independently H, or a group selected from an alkyl, alkenyl, aryl, hydroxyle, halogen, alkoxy, carboxylate.

In another preferred embodiment, -L$_B$-M$_B$ may be represented by

[chemical structure]

wherein q is as defined above, preferably q is equal to 3 s is an integer ranging from 1 to 5, preferably s is equal 2, 3 or 4, t is 1 or 2, R$_{14}$ and R$_{15}$ are each independently H, or a group selected from an alkyl, alkenyl, aryl, hydroxyle, halogen, alkoxy, carboxylate, X$_1$, X$_2$ and X$_3$ are each independently N or C, the bounds represented by a dotted line being each independently either absent or present, R$_{12}$, R$_{16}$, R$_{17}$, R$_{18}$, R$_{19}$, R$_{20}$ and R$_{21}$ are each independently H, or a group selected from an alkyl, alkenyl, aryl, hydroxyle, halogen, alkoxy, carboxylate, or may be absent when the bound represented by a dotted line is present.

In a preferred embodiment -L$_B$-M$_B$ is

[chemical structure]

wherein q is as defined above.

In a preferred embodiment $-L_B-M_B$ is

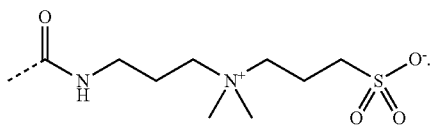

In one embodiment of the invention, the ligand has a molecular weight from about 1,000 g/mol to about 200,000 g/mol, preferably from about 1,000 g/mol to about 100,000 g/mol, preferably from about 1,000 g/mol to about 50,000 g/mol, from about 5,000 g/mol to 50,000 g/mol, more preferably from about 1,000 g/mol to about 10,000 g/mol, from about 5,000 g/mol to 10,000 g/mol.

In one embodiment of the invention, the ligand has a polydispersity index inferior to 5, preferably inferior to 3.

In one embodiment of the invention, the ligand has a ratio of monomers A/B in number from about 1/99 to about 99/1. In a particular embodiment, the ligand has a ratio of monomers A/B in number from about 1/99 to about 50/50, preferably from about 3/97 to about 40/60, more preferably about 7/93. In another particular embodiment, the ligand has a ratio of monomers A/B in number from about 50/50 to about 99/1, preferably from about 40/60 to about 90/10. In another embodiment, the ligand has a ratio of monomers A/B in number from about 1/99 to about 75/25, preferably from about 5/95 to about 50/50, more preferably from about 5/95 to about 25/75.

According to one embodiment, the synthesis of the ligand may be performed in presence of monomer A and monomer B with a ratio of molar amounts of A to B ranging from 1/99 to 99/1, preferably from 5/95 to 50/50, preferably from 10/90 to 30/70, more preferably 20/80.

According to one embodiment, the synthesis of the ligand may be performed by controlled radical polymerization such as RAFT polymerization (Radical Addition-Fragmentation chain Transfer) or non-controlled radical polymerization.

According to one embodiment, the synthesis of the ligand may be performed in presence of a monomer A and monomer B and a solvent such as for example THF, water or a mixture thereof.

In a preferred embodiment, the solvent is a mixture of THF and water, preferably a 1:1 mixture.

In one embodiment, the polymerization of monomers A and B is initiated by an initiator such as for example 2,2'-azobis(2-methylpropionamidine).

In one embodiment, the polymerization of monomers A and B is terminated by a terminator such as for example 3-mercaptopropionic acid.

In one embodiment, the molar quantity of the initiator is ranging from 5 to 15%, preferably 10%, in moles relative to the molar amount of monomers.

In one embodiment, the molar quantity of the terminator is ranging from 0.1 to 15%, from 1% to 15%, from 2% to 15%, from 5% to 15% in moles relative to the molar amount of monomers. In another embodiment, the molar quantity of the terminator is 10% in moles relative to the molar amount of monomers.

In another embodiment of the invention, said ligand is a copolymer synthesized from at least 3 monomers, said monomers being:
one anchoring monomer as defined here above,
one hydrophilic monomer as defined here above, and
one functionalizable monomer comprising a reactive function $M_C$.

In one embodiment of the invention, said ligand has the following formula III:

$$(A)_x(B)_y(C)_z,$$

wherein
A comprises at least one anchoring monomer comprising a first moiety $M_A$ having affinity for the surface of a nanocrystal as described here above,
B comprises at least one hydropohilic monomer comprising a second moiety $M_B$ having a high water solubility,
C comprises at least one functionalizable monomer comprising a third moiety $M_C$ having a reactive function, and
each of x, y and z is independently a positive integer, preferably an integer ranging from 1 to 498.

In one embodiment, each of x, y and z is independently a positive integer, preferably an integer selected in the group of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30.

In said embodiment, said ligand has the following formula IV:

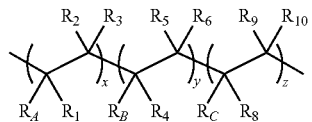

wherein
$R_A$, $R_B$, $R_1$, $R_2$, $R_3$, $R_4$, $R_5$ and $R_6$ are defined here above,
$R_C$ represents a group comprising the third moiety $M_C$, and
$R_8$, $R_9$ and $R_{10}$ can be independently H, or a group selected from an alkyl, alkenyl, aryl, hydroxyl, halogen, alcoxy, carboxylate,
each of x, y and z is independently a positive integer, preferably an integer ranging from 1 to 498.

In one embodiment, each of x, y and z is independently a positive integer, preferably an integer selected in the group of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30.

In one embodiment of the invention, x+y+z is ranging from 5 to 750, 5 to 500, 5 to 150, 5 to 100, 10 to 75, 10 to 50, 5 to 50, 15 to 25, 5 to 25.

In one embodiment of the invention, $R_2$, $R_3$, $R_5$ $R_6$, $R_9$ and $R_{10}$ are H.

In one embodiment of the invention, $R_1$, $R_4$ and $R_8$ are alkyl groups, preferably methyl.

In one embodiment of the invention, said third moiety $M_C$ having a reactive function can form a covalent bond with a selected agent under selected conditions and includes, but is not limited to, any moiety having an amine group such as a primary amine group, any moiety having an azido group, any moiety having an halogen group, any moiety having an alkenyl group, any moiety having an alkynyl group, any moiety having an acidic function, any moiety having an activated acidic function, any moiety having an alcoholic group, any moiety having an activated alcoholic group, any moiety having a thiol group. It can also be a small molecule, such as biotin, that can bind with high affinity to a macromolecule, such as a protein or an antibody.

According to one embodiment, the reactive function of $M_C$ may be protected by any suitable protective group commonly used in the chemical practice. Protection and deprotection may be performed by any suitable method known in the art and adapted to the structure of the molecule to be protected. The reactive function of $M_C$ may be protected during the synthesis of the ligand and removed after the polymerization step. The reactive group of $M_C$ may alternatively be introduced in the ligand after the polymerization step.

In another embodiment of the invention, said third moiety $M_C$ having a reactive function can form a non covalent bond with a selective binding counterpart and said third moiety $M_C$ having a reactive function includes, but is not limited to, biotin that binds its counterpart streptavidin, a nucleic acid that binds its counterpart a sequence-complementary nucleic acid, FK506 that binds its counterpart FKBP, an antibody that binds its counterpart the corresponding antigen.

In one embodiment of the invention, $R_C$ comprising the third moiety $M_C$ can have the formula $-L_C-M_C$, wherein $L_C$ can be a bond or an alkylene, alkenylene, a PEG moiety, or arylene linking group having 1 to 8 chain atoms and can be optionally interrupted or terminated by —O—, —S—, —NR$_7$—, wherein $R_7$ is H or alkyl, —CO—, —NHCO—, —CONH— or a combination thereof and $M_C$ corresponds to the third moiety as described here above. An example of a suitable PEG moiety is —[O—CH$_2$—CHR']$_n$—, wherein R' can be H or $C_1$-$C_3$ alkyl, and n can be an integer in the range of 0 to 30.

Preferably, $L_C$ is —C(=O)—NH—(CH$_2$)$_r$—, wherein r is an integer ranging from 1 to 5, preferably 2, 3, 4.

In a preferred embodiment, $-L_C-M_C$ is

[chemical structure: acyl-NH-(CH$_2$)$_r$-M$_C$]

wherein r and $M_c$ are as defined above, preferably r is equal to 3.

In a preferred embodiment, $-L_C-M_C$ may be represented by

[chemical structure: acyl-NH-(CH$_2$)$_r$-R$_{11}$]

wherein r is as defined above and $R_{11}$ is a group selected from amine, —NH$_2$, —N$_3$, alkenyl group or —COOH.

In a preferred embodiment, r is equal to 3 and $R_{11}$ is —NH$_2$.

In a preferred embodiment $-L_C-M_C$ is

[chemical structure: acyl-NH-(CH$_2$)$_3$-NH$_2$]

In one embodiment of the invention, the ligand has a ratio of monomers A/B/C from about 1/94/5 to about 30/55/15, preferably from about 10/80/10 to about 25/60/15, more preferably about 20/70/10.

According to one embodiment, the synthesis of the ligand may be performed in presence of monomer A, monomer B and monomer C with a ratio of molar amounts of A/B/C ranging from about 10/85/5 to 25/60/15, preferably 20/70/10.

In another embodiment of the invention, said ligand has the following formula IV':

[chemical structure of formula IV' with labels $R_2'$, $R_3'$, $R_2''$, $R_3''$, $R_5'$, $R_6'$, $R_5''$, $R_6''$, $R_9'$, $R_{10}'$, $R_9''$, $R_{10}''$ on top and $R_A'$, $R_1'$, $R_A''$, $R_1''$, $R_B'$, $R_4'$, $R_B''$, $R_4''$, $R_C'$, $R_8'$, $R_C''$, $R_8''$ on bottom with x', x", y', y", z', z" segments]

wherein
$R_A'$, $R_A''$, $R_B'$, $R_B''$, $R_1'$, $R_2'$, $R_3'$, $R_1''$, $R_2''$, $R_3''$, $R_4'$, $R_5'$, $R_6'$, $R_4''$, $R_5''$, and $R_6''$ are defined here above, $R_C'$ and $R_C''$ represent respectively a group comprising the third moiety $M_C'$ and $M_C''$, and $R_8'$, $R_9'$, $R_{10}'$, $R_8''$, $R_9''$, and $R_{10}''$ can be independently H, or a group selected from an alkyl, alkenyl, aryl, hydroxyl, halogen, alcoxy, carboxylate, each of x' and x" is independently a positive integer, preferably an integer ranging from 0 to 499, with the condition that at least one of x' and x" is not 0, each of y' and y" is independently a positive integer, preferably an integer ranging from 0 to 499, with the condition that at least one of y' and y" is not 0, each of z' and z" is independently a positive integer, preferably an integer ranging from 0 to 499, with the condition that at least one of z' and z" is not 0.

In one embodiment, each of x' and x" is independently a positive integer, preferably an integer selected in the group of 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, with the condition that at least one of x' and x" is not 0.

In one embodiment, each of y' and y" is independently a positive integer, preferably an integer selected in the group of 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, with the condition that at least one of y' and y" is not 0.

In one embodiment, each of z' and z" is independently a positive integer, preferably an integer selected in the group of 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, with the condition that at least one of z' and z" is not 0.

In one embodiment of the invention, x'+x"+y'+y"+z'+z" is ranging from 5 to 750, 5 to 500, 5 to 150, 5 to 100, 10 to 75, 10 to 50, 5 to 50, 15 to 25, 5 to 25.

In one embodiment of the invention, $R_2'$, $R_3'$, $R_2''$, $R_3''$, $R_5'$, $R_6'$, $R_5''$, $R_6''$, $R_9'$, $R_{10}'$, $R_9''$ and $R_{10}''$ are H.

In one embodiment of the invention, $R_1'$, $R_1''$, $R_4'$, $R_4''$, $R_8'$ and $R_8''$ are alkyl groups, preferably methyl.

In one embodiment of the invention, said moiety $M_C$ comprises said moieties $M_C'$ and $M_C''$.

In one embodiment of the invention, said z is equal to z'+z".

Another object of the invention is a ligand which is a copolymer functionalized with a molecular probe and/or a targeting group.

Preferably, the copolymer is functionalized with a molecular probe and/or a targeting group on $M_C$.

Examples of said targeting group include, but are not limited to, avidin, streptavidin, fluorescein, an antibody, a single chain antibody, a polyhistidine tag, a protein or peptide sequence having a specific binding affinity for an affinity target, such as for example an avimer or an affibody (the affinity target may be for example a protein, a nucleic acid, a peptide, a metabolite or a small molecule), antigens, steroids, vitamins, drugs, haptens, metabolites, toxins, environmental pollutants, amino acids, peptides, proteins, aptamers, nucleic acids, nucleic acid polymers, folates, carbohydrates, lipids, phospholipid, lipoprotein, lipopolysaccharide, liposome hormone, polysaccharide, and polymers.

In one embodiment of the invention, said ligand may be a copolymer functionalized with a plurality of molecular probes and/or targeting groups, which may be the same or different.

Another object of the invention is a nanocrystal complexed with at least one ligand of the invention.

In one embodiment, said nanocrystal is a 0D, 1D, or 2D nanocrystal.

In one embodiment, said nanocrystal may be for instance a nanosheet, a nanorod, a nanoplatelet, a nanoplate, a nanoprism, a nanowall, a nanodisk, a nanoparticle, a nanowire, a nanopowder, a nanotube, a nanotetrapod, a nanoribbon, a nanobelt, a nanoneedle, a nanocube, a nanoball, a nanocoil, a nanocone, a nanopiller, a nanoflower, or a quantum dot.

In one embodiment, said nanocrystal can be a sphere, a cube, a tetrahedron, a rod, a wire, a platelet, a tube, a cube, a ribbon or other shape.

In one embodiment, said nanocrystal is inorganic.

In one embodiment, said nanocrystal is organic.

In one embodiment, said nanocrystal is a semiconductor material, a ceramic material, a magnetic material or a metallic material.

In one embodiment, said nanocrystal is a semi-conductor selected from group IV, group IIIA-VA, group IIA-VIA, group IIIA-VIA, group IA-IIIA-VIA, group IIA-VA, group IVA-VIA, group VIB-VIA, group VB-VIA, or group IVB-VIA.

In one embodiment, said nanocrystal is a material MxEy, wherein

M is Zn, Cd, Hg, Cu, Ag, Al, Ga, In, Si, Ge, Pb, Sb, Pd, Fe, Au, Ti, Bi, W, Mo, V or a mixture thereof, E is O, S, Se, Te, N, P, As, or a mixture thereof, and x and y are independently a decimal number from 0 to 5, at the condition that when x is 0, y is not 0 and inversely.

In one embodiment, said material MxEy comprises cationic elements M and anionic elements E in stoichiometric ratio, said stoichiometric ratio being characterized by values of x and y corresponding to absolute values of mean oxidation number of elements E and M respectively.

In one embodiment, said nanocrystal is a material selected from Si, Ge, CdS, CdSe, CdTe, ZnS, ZnSe, ZnTe, HgS, HgSe, HgTe, PbS, PbSe, PbTe, CuInS$_2$, CuInSe$_2$, AgInS$_2$, AgInSe$_2$, CuS, Cu$_2$S, Ag$_2$S, Ag$_2$Se, Ag$_2$Te, InN, InP, InAs, InSb, In$_2$S$_3$, Cd$_3$P$_2$, Zn$_3$P$_2$, Cd$_3$As$_2$, Zn$_3$As$_2$, ZnO, AlN, AlP, AlAs, AlSb, GaN, GaP, GaAs, GaSb, FeS$_2$, TiO$_2$, Bi$_2$S$_3$, Bi$_2$Se$_3$, Bi$_2$Te$_3$, MoS$_2$, WS$_2$, VO$_2$, and alloys and mixtures thereof.

In one embodiment, said nanocrystal is a metallic material such as gold, silver, copper, aluminum, iron, platinum, lead, palladium, iron oxide, titanium dioxide, cerium oxide, metal chalcogenide, metal pnictide, cadmium, zinc, magnesium, mercury, gallium, indium, thallium, cobalt, tin or mixtures thereof.

In one embodiment, said nanocrystal presents a heterostructure, which means that the nanocrystal of the invention is partially coated by at least one layer of inorganic material.

A semiconductor nanocrystal is capable of emitting electromagnetic radiation upon excitation (i.e., the semiconductor nanocrystal is luminescent) and includes a "core" of one or more first semiconductor materials, and may be surrounded by a "shell" of a second semiconductor material. A semiconductor nanocrystal core surrounded by a semiconductor shell is referred to as a "core/shell" semiconductor nanocrystal. The surrounding "shell" material will preferably have a bandgap energy that is larger than the bandgap energy of the core material and may be chosen to have an atomic spacing close to that of the "core" substrate.

In one embodiment, the nanocrystal of the invention presents a core/shell structure, i.e. the nanocrystal comprises a core and a shell of semiconducting material.

In one embodiment, the nanocrystal of the invention has a core/shell structure, i.e. the core is totally coated by at least one layer of inorganic material.

Preferably, said quantum dots are core/shell type I quantum dots. Said type I quantum dot can have a band alignment between the core and the shell such that the exciton created in the shell is transferred in the core where it recombines radiatively.

In another embodiment, the nanocrystal of the invention comprises a core totally coated by a first layer of inorganic material, said first layer being partially or totally surrounded by at least one further layer of inorganic material.

In one embodiment, said core and said at least one layer of inorganic material have the same composition or do not have the same composition.

In one embodiment, said core and said at least one layer of inorganic material may be a semi-conductor from group IV, group IIIA-VA, group IIA-VIA, group IIIA-VIA, group IA-IIIA-VIA, group IIA-VA, group IVA-VIA, group VIB-VIA, group VB-VIA, or group IVB-VIA.

In another embodiment, said core and said at least one layer of inorganic material may comprise a material MxEy, wherein M is Zn, Cd, Hg, Cu, Ag, Al, Ga, In, Si, Ge, Pb, Sb, Pd, Fe, Au, Ti, Bi, W, Mo, V or a mixture thereof, E is O, S, Se, Te, N, P, As, or a mixture thereof, and x and y are independently a decimal number from 0 to 5, at the condition that when x is 0, y is not 0 and inversely.

In another embodiment, said core and said at least one layer of inorganic material may be composed of a material from Si, Ge, CdS, CdSe, CdTe, ZnS, ZnSe, ZnTe, HgS, HgSe, HgTe, PbS, PbSe, PbTe, CuInS$_2$, CuInSe$_2$, AgInS$_2$, AgInSe$_2$, CuS, Cu$_2$S, Ag$_2$S, Ag$_2$Se, Ag$_2$Te, InN, InP, InAs, InSb, In$_2$S$_3$, Cd$_3$P$_2$, Zn$_3$P$_2$, Cd$_3$As$_2$, Zn$_3$As$_2$, ZnO, AlN, AlP, AlAs, AlSb, GaN, GaP, GaAs, GaSb, FeS$_2$, TiO$_2$, Bi$_2$S$_3$, Bi$_2$Se$_3$, Bi$_2$Te$_3$, MoS$_2$, WS$_2$, VO$_2$, and alloys and mixtures thereof.

In one embodiment, the core and/or the shell can be a semiconductor material including, but not limited to, those of the group II-VI (ZnS, ZnSe, ZnTe, CdS, CdSe, CdTe, HgS, HgSe, HgTe, MgS, MgSe, MgTe, CaS, CaSe, CaTe, SrS, SrSe, SrTe, BaS, BaSe, BaTe, and the like) and III-V (GaN, GaP, GaAs, GaSb, InN, InP, InAs, InSb, and the like) and IV (Ge, Si, and the like) and IV-VI (PbS, PbSe) and I-III-VI-2 (CuInS2, CuInSe2, AgInS2, AgInSe2, CuGaS2, CuGaSe2, AgGaS2, AgGaSe2) and L2-VI (Ag2S, Ag2Se) and IV-VI-2 (SnS2, SnSe2) and II-V (Cd3P2) and oxides (ZnO) materials, and an alloy or a mixture thereof.

In another embodiment, the nanocrystal of the invention presents a heterostructure comprising a metallic material and semiconductor material.

In an embodiment of the invention, said nanocrystal may be further surrounded by a "coat" of an organic capping agent. The organic capping agent may be any material, but has preferably an affinity for the nanocrystal surface. In general, the capping agent can be an isolated organic molecule, a polymer (or a monomer for a polymerization reaction), and an extended crystalline structure.

In one embodiment, said organic capping agents are selected from trioctylphosphine oxide, organic thiols, amines, phosphines, carboxylic acids, phosphonic acids, sulfonic acids, trialkoxysilanes, alkyl and aryl halides; and mixtures thereof.

In another embodiment of the invention, said nanocrystal may be further surrounded by a "coat" of an inorganic capping agent. In one embodiment, the inorganic capping agent comprises an inorganic complex, an extended crystalline structure, metals selected from transition metals, lanthanides, actinides, main group metals, metalloids, and mixture thereof.

In one embodiment, the inorganic capping agent comprises ionic salts.

In another embodiment, the nanocrystal of the invention may be surrounded by a mixture of inorganic and organic capping agent.

In one embodiment, the nanocrystal of the present invention has at least one dimension having a size of about 0.3 nm to less than 10 mm, about 0.3 nm to about 1 µm, about 0.5 nm to about 700 nm, about 1 nm to about 500 nm, about 1.5 nm to about 200 nm, about 2 nm to about 100 nm.

In one embodiment, the nanocrystal of the present invention has a thickness of about 0.3 nm to about 10 mm, about 0.3 nm to about 1 mm, about 0.3 nm to about 100 µm, about 0.3 nm to about 10 µm, about 0.3 nm to about 1 µm, about 0.3 nm to about 500 nm, about 0.3 nm to about 250 nm, about 0.3 nm to about 150 nm, about 0.3 nm to about 100 nm, about 0.3 nm to about 50 nm, about 0.3 nm to about 40 nm, about 0.3 to about 30, about 0.3 nm to about 25 nm, about 0.3 nm to about 20 nm, about 0.3 nm to about 10 nm, about 0.3 nm to about 5 nm, about 0.3 nm to about 2 nm.

In one embodiment, the nanocrystal of the present invention has its lateral dimensions larger than its thickness.

In one embodiment, the nanocrystal of the present invention has a lateral dimension (length and/or width) of at least 1.5 times its thickness.

In another embodiment, the lateral dimensions of the nanocrystal are at least 2, 2.5, 3, 3.5, 4, 4.5, 5 times larger than its thickness.

In another embodiment of the invention, the lateral dimensions of the nanocrystal are at least 2, 2.5, 3, 3.5, 4.5, 5, 6, 7, 8, 9, 10 times larger than the thickness.

In another embodiment of the invention, the lateral dimensions of the nanocrystal of the invention are at least 20, 30, 40, 50, 60, 70, 80, 90, 100, 150, 200, 250, 300, 350, 400, 450, 500 times larger than the thickness.

In one embodiment, the lateral dimensions of the nanocrystal are from at least 0.45 nm to at least 50 mm.

In one embodiment, the lateral dimensions of the nanocrystal are from at least 2 nm to less than 1 m, from 2 nm to 100 mm, from 2 nm to 10 mm, from 2 nm to 1 mm, from 2 nm to 100 µm, from 2 nm to 10 µm, from 2 nm to 1 µm, from 2 nm to 100 nm, from 2 nm to 50 nm, from 2 nm to 25 nm, from 2 nm to 20 nm, from 2 nm to 15 nm, from 2 nm to 10 nm, from 2 nm to 8 nm, from 2 nm to 6 nm.

In one embodiment of the invention, examples of the nanocrystal of the invention include, but are not limited to, nanosheet of CdSe with a shell of CdS or ZnS (having a quantum yield superior to 60% and a narrow FHWM (less than 20 nm)), nanosheet of CdS coated with ZnS (CdS/Zns), nanosheet of CdSexS1-x (x being a decimal number from 0 to 1) coated with CdyZn1-yS (y being a decimal number from 0 to 1) (CdSeS/CdZnS), nanosheet of CdSexSe1-x (x being a decimal number from 0 to 1) coated with ZnS (CdSeS/ZnS), nanosheet of CdTe coated with CdyZn1-ySexS1-x ((x and y being independently a decimal number from 0 to 1) CdTE/CdZnSeS), nanosheet of CdS coated with ZnS doped with Manganese II or Copper II CdS/ZnS:Mn or CdS/ZnS:Cu.

Preferably, the nanocrystal of the invention is selected in the group comprising CdSe, CdTe, CdS, and the core/shell structures such as CdSe/CdS, CdSe/CdZnS, CdTe/CdS/CdZnS, CdS/ZnS.

As used here above, the term nanoplatelets (NPLs) (or nanosheets) refers to an inorganic crystallite having its lateral dimensions larger than its thickness.

These NPL present a good resistance to photobleaching, very fast fluorescence lifetimes (few hundreds of picoseconds to few nanoseconds), high quantum yield (up to 50%) and surprisingly, its absorption cross section can be tuned to arbitrarily large values while its emission wavelength remains unchanged. The increase of the absorption cross section is related to the lateral dimension of the NPL. Its emission wavelength is related to its thickness and its composition. Emission wavelength and absorption cross section can thus be tuned completely independently.

Another object of the invention is a method for complexing at least one ligand of the invention to at least one nanocrystal, comprising:
  optionally a first step of complexation of nanocrystals with an intermediate ligand being a weakly binding ligand or a small molecule (Meerwein's salt) ensuring the solubilization of the nanocrystal into a solvent miscible in part with water,
  a step of monophasic exchange at about 40° C. to about 100° C. in an aqueous medium overnight to remove the weak intermediate ligand and replace it by the ligand of the invention.

In one embodiment, said weakly binding ligand or molecule may be MPA, or trimethylsilylating agents, or trialkyl oxonium salts (Meerwein's salt), or any monothiol, or amine ligands.

In one embodiment, said first step is performed in basic chloroform and leads to the precipitation of the nanocrystal complexed to the intermediate ligand and to the solubilization of the nanocrystal into water at room temperature.

In one embodiment, said second step is performed in an aqueous medium such as 20 mM aqueous NaCl at about 50° C. to 75° C., preferably 65° C., overnight, to remove the weak intermediate ligand and replace it by the ligand of the invention.

In another embodiment, said method may further comprise an ultrafiltration step and then an ultracentrifugation step in an aqueous sucrose gradient.

Another object of the invention is a water-soluble composition comprising at least one quantum dot, nanoplatelet or quantum dot having its lateral dimensions larger than its thickness, complexed with at least one ligand of the invention.

Another object of the invention is the use of said quantum dot, nanoplatelet or quantum dot having its lateral dimensions larger than its thickness, complexed with at least one ligand of the invention for bioimaging, biotargeting, medical imaging, biosensing.

Thus, it is readily apparent that said complexes find use in a variety of assays where other, less reliable, labeling methods have typically been used, including, without limitation, fluorescence microscopy, fluorescence histology, fluorescence cytology, fluorescence pathology, cell labeling, flow cytometry, western blotting, Fluorescence Resonance Energy Transfer (FRET), immunocytochemistry, Fluorescence In Situ Hybridization (FISH) and other nucleic acid hybridization assays, signal amplification assays, DNA and protein sequencing, immunoassays such as competitive binding assays and ELISAs, immunohistochemical analysis, protein and nucleic acid separation, homogeneous assays, multiplexing, high throughput screening, chromosome karyotyping, and the like.

EXAMPLES

Figure 1:
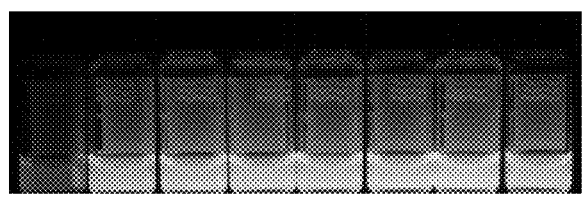
FIG. 1: L2-QDs in pH 2, 3, 5, 7, 9, 11, 13 and saturated NaCl aqueous solutions (from left to right) under a 302-nm UV light (>12 months).

The present invention is further illustrated by the following examples.

Ligand design and synthesis. To answer the need of increasing ligand affinity for the nanocrystal surface, we directed our efforts towards ligands exhibiting several attachments points and turned logically to polymerization. We thus synthesized a hydrophilic polymer, L2, derived from the small molecule L1 presented above and resulting from a two-step process (Scheme 2). The first step consisted in the radical random copolymerization of two methacryl-amides: one containing the precursor of the dithiol anchoring function (monomer A, obtained from the peptidic coupling between thioctic acid and N-(3-aminopropyl) methacrylamide), the other including the sulfobetaine group (monomer B, commercially available). Due to mismatching monomer solubilities, the solvent had to be adjusted to THF/water 1/1 (v/v) and the A/B ratio was optimized to a maximum of 20/80 to provide a water-soluble polymer. Note that the amounts of initiating (2,2'-azobis(2-methylpropionamidine)dihydrochloride, V50) and terminating (3-mercaptopropionic acid, MPA) agents were both chosen equal to 10% molar equivalents relative to the total amount of monomers, in order to prevent the formation of too long chains, thus keeping a small ligand size. The reaction led thereby to bipolymer b-L2 (for "bridged-L2") in 70% yield.

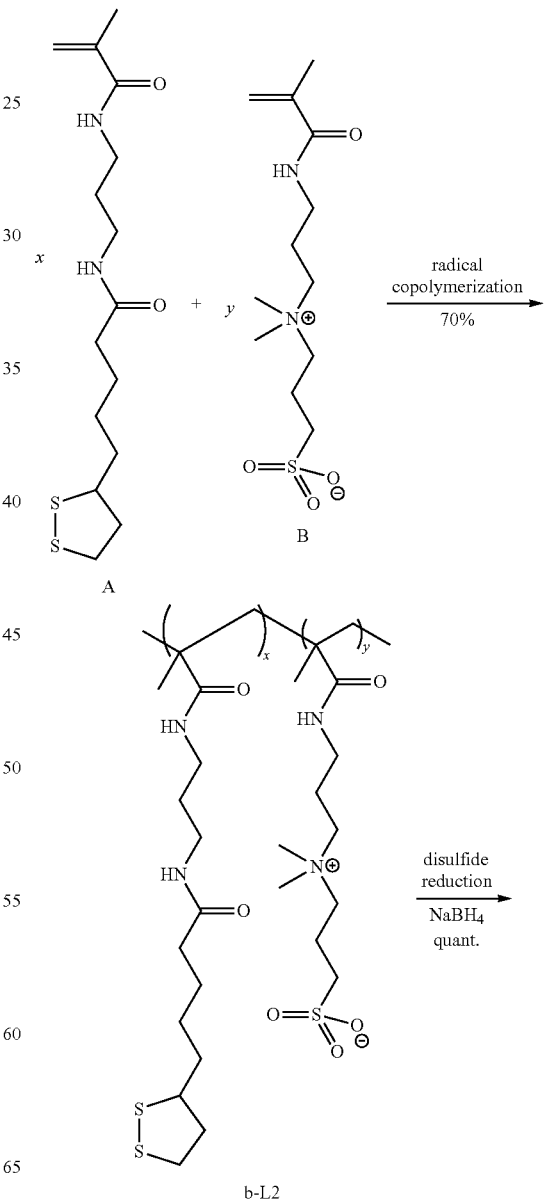

Scheme 2. Ligand L2 synthesis.

-continued

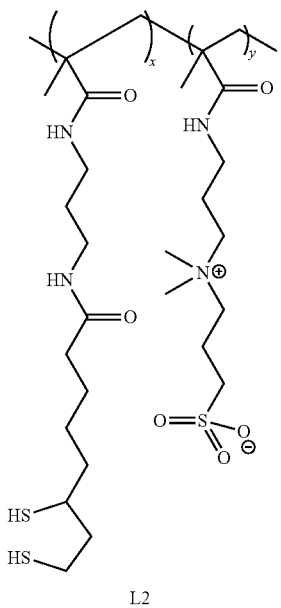

L2

Then, in a second step, b-L2 was treated by sodium borohydride in water to reduce its disulfide bridge and free the anchoring thiol groups, giving the corresponding polymer L2 (initial A/B ratio=20/80).

Another polymer, L3, was synthesized this way, using an initial A/B molar ratio equal to 10/90.

Characterization of the products by gel permeation chromatography in water (Viscotek GPCmax, triple detection) confirmed the expected low number average molecular weights (5,000<$\overline{M}_n$<8,000 g·mol$^{-1}$, i.e. ≈15-25 monomers per chain, for all synthesized polymers) and showed polydispersity indexes (PDI=$M_w/M_n$) below 3. The dosage of the dithiol functions using Ellman's method allowed, in turn, an estimation of the effective A/B ratio in the polymeric samples: 7/93 for L2 and 2/98 for L3. These A/B ratios are quite different from the initial ratios, probably due to differences in reactivity between the two monomers.

The bipolymers were stored under their oxidized bridged form (b-L2, b-L3) and their reduction was carried out just before any ligand exchange procedure.

Ligand exchange. The synthesized polymers were then dissolved in water and tested in a "classical" biphasic cap exchange with CdSe/CdS/ZnS core/shell QDs solubilized in chloroform. Surprisingly, the nanoparticles were extracted from the organic phase, but did not get into water, remaining at the interface. We attributed this observation to the poor solubility of the polymer in chloroform: it implies a low partition coefficient between the two solvents and a difficult phase transfer of the QDs. To overcome this problem, we moved to a two-step process. A first monophasic exchange using a small monodentate hydrophilic ligand, namely MPA, on as-synthesized QDs in basic chloroform, led to the precipitation of MPA-QDs and allowed the solubilization of the QDs into water at room temperature. Then, a second step, still monophasic, consisted in the removal of the weak intermediate ligand MPA from the QDs and its replacement by our polymer in an aqueous medium at 65° C. overnight.

After purification of polymer L2-capped QDs by ultrafiltration then ultracentrifugation in an aqueous sucrose gradient, the physical properties of the nanoparticles were characterized by fluorescence spectroscopy and DLS. The nanocrystals showed a slightly reduced quantum yield (in the range of 30-40%, compared to 50-60% before cap exchange) and a suitable small size (15-18 nm as hydrodynamic diameter, for a core/shell diameter of 6-7 nm).

L2-QDs were then subjected to a series of stability experiments to confirm the multiplication of anchoring and hydrophilic functions has a significant influence on the QD colloidal stability as well as on the ligand stability onto the nanoparticles itself.

Stability versus pH and salinity. First, saline L2-QDs aqueous solutions (≈0.6 μM in 3 M aqueous NaCl) proved to be very stable over a large pH range, more precisely from pH 3 to 13, during several months and at 4° C. (>10 months, FIG. 1). The charges of the pending sulfobetaine groups of polymer L2, responsible for its hydrophilicity and for the colloidal stability of the corresponding QDs in water, are indeed insensitive to pH. Moreover, they could stand high salinity conditions, up to a saturated aqueous NaCl solution (≈6 M), indefinitely. These properties are explained by the zwitterionic nature of the sulfobetaine groups whose charges are screened by ionic species, so that the attractive interaction between zwitterions is masked and the solvation of the corresponding polymer increases with the ionic strength. This specific feature constitutes a great advantage, compared to poly(ethylene glycol)-coated QDs, which can hardly stand highly saline media. In addition, this proves solubilizing zwitterionic QDs in highly saline or even saturated solutions can be a very convenient long-time storage method, even if the samples are diluted.

Such a test is very common in the literature discussing QD surface chemistry, since stable samples are evidences of a good surface passivation. But it is only a pre-requisite and it is far from being enough to demonstrate QD stability in the conditions of a bio-imaging experiment, which are not only highly diluted, but also less saline and much warmer (37° C.), i. e. much less favorable than those used in this experiment.

Figure 2:
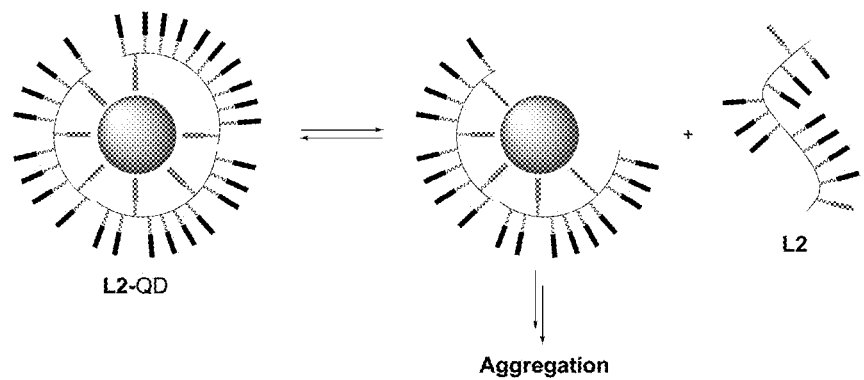
FIG. 2: Principle of the dilution experiment to test L2-QD colloidal stability.

Stability versus dilution. Hence the affinity of the ligands for the QDs was tested through dilution experiments: QD samples were diluted to concentrations being in the range of 0.3 μM in 20 mM aqueous NaCl and left at room temperature. In such conditions, the adsorption/desorption equilibrium existing between the capping ligand and the surface of QDs is shifted towards ligand desorption, so that ligand concentration in solution is homogenized (moderation principle). QDs lose their colloidal stability consequently and begin to aggregate (FIG. 2).

Aggregation kinetics can therefore be monitored by the measurement of QDs' remaining absorbance in solution. Practically, the samples were centrifuged (16,000 g, 5 min) to remove aggregates and the absorbance at 350 nm of the corresponding supernatant was measured, this procedure being repeated over time. The influence of two parameters was underlined by our results: the type of capping ligand (L1, L2, L3) and the temperature of the second exchange step (polymer/QD) in water.

Figure 3:
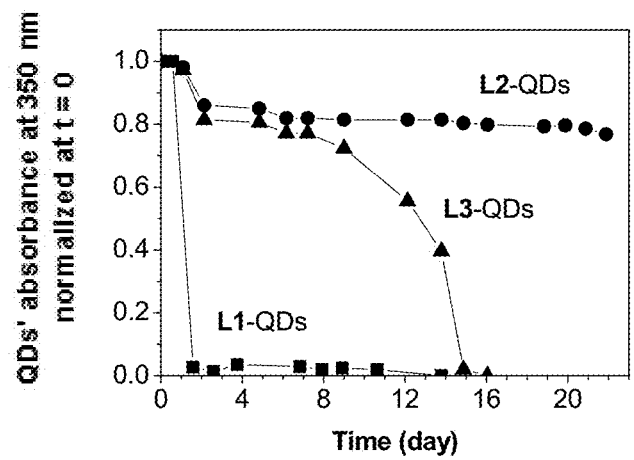
FIG. 3: Influence of the capping ligand on QD colloidal stability (exchange conditions: 65° C./overnight; dilution experiment conditions: 0.3 µM in 20 mM aqueous NaCl).

To counter the desorption process, QD-ligand affinity must be as strong as possible. FIG. 3 clearly shows that an increasing number of anchoring functions per ligand prevents the aggregation of the nanoparticles (absorbance decrease with time slows down in the series L1, L3, L2), thus improving QD colloidal stability. More accurately, in the case of our polymers, we believe that the amount of dithiol functions per ligand bound to the QDs must be much greater than suggested by Ellman's assay. As the PDI are higher than 1 and the monomer distributions can vary throughout the polymeric chains, a sorting of the ligands can occur during the exchange step, to the benefit of the chains including the largest number of dithiols, which are therefore more stable. Note that the absorbance of the QDs coated with polymer L2 remained above 75% of the initial absorbance, even after a 20-day experiment under diluted conditions. This demonstrates a remarkable improvement of the colloidal stability over time, compared to L3-QDs, which lost their stability after 15 days and especially, compared to bidentate-ligand-L1-coated QDs, which precipitated in less than 2 days.

Figure 4:
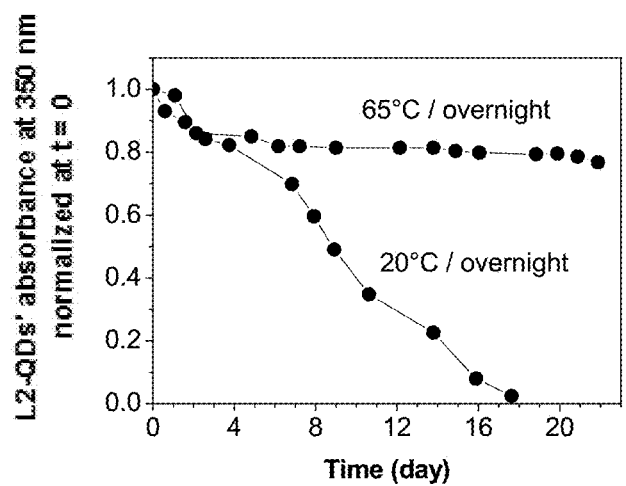
FIG. 4: Influence of the exchange (L2/QD) temperature on colloidal stability of L2-QDs (dilution experiment conditions: 0.3 µM in 20 mM aqueous NaCl).

Another relevant point is the role of the temperature of the aqueous final ligand exchange step. As shown by FIG. 4 in the case of the exchange reaction with L2, heating is required to produce nanoparticles stable against dilution. This finds its explanation in the competition which takes place during the exchange reaction, between the original and the polymeric ligands on one hand, and among the polymer molecules themselves on the other hand. An elevated temperature is needed to displace native ligands and replace them by the new ones, so that the QDs acquire a good colloidal stability; it can also be necessary to allow the longest chains, which are less mobile but enriched in linking functions, to bind to QDs in a thermodynamically controlled process.

These experiments were repeated on several QD and polymer syntheses batches and proved to be highly reproducible. Nevertheless, some slight variations in stability can occur, but only after very long times of experiment (>1 month).

After these characterizations of L2-QD colloidal stability, we wanted to understand it better and verify to which extent it could be attributed to the affinity of ligand L2 for the surface of the QDs.

Stability versus a competing ligand. To further test the stability of L2 onto QDs and demonstrate the adaptability of the polymeric synthesis to diverse applications, we introduced a monomer including a functional group during the polymerization process. Monomer C, bearing a reactive amine end function, was added to and copolymerized with methacrylamides A and B, in an A/B/C ratio equal to 20/70/10, to give, after disulfide reduction, terpolymer L2-$NH_2$. As an illustration, this functionalizable polymer could be coupled to a fluorescein carboxylic derivative and then, exchanged with QDs (Scheme 3). Absorbance measurements on these L2-fluorescein-QDs let us estimate a number of ten functionalizable amines per nanoparticle, after subtraction of QD characteristic absorbance.

Scheme 3. Synthesis of ligand L2-fluorescein and QD functionalization.

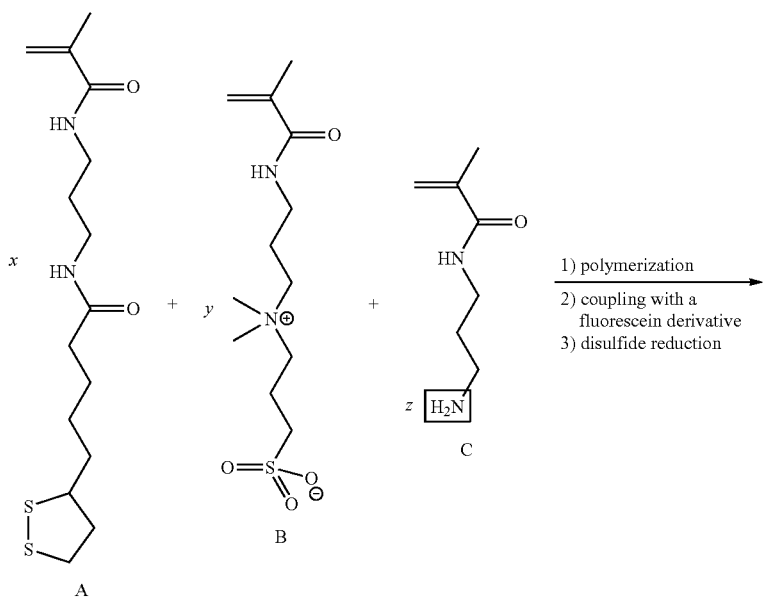

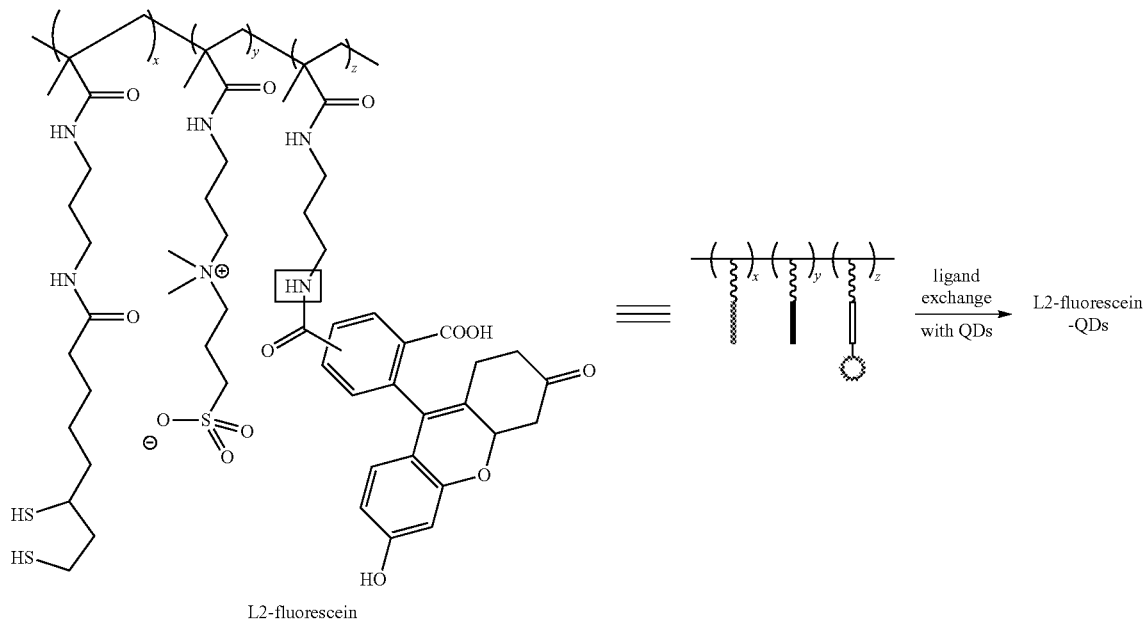

L2-fluorescein

Figure 5:
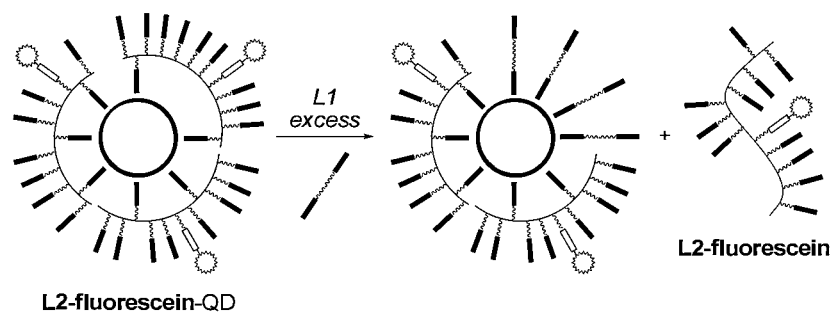
FIG. 5: Principle of the L2 vs L1 competition experiment.

These functionalized QDs proved to be particularly useful in the determination of L2-fluorescein—which is a modified L2-type ligand—stability at the surface of QDs. To L2-fluorescein-QDs was opposed a 10,000-fold molar excess of competing ligand L1 (FIG. 5). In these conditions, and due to ligand adsorption/desorption dynamic equilibrium, re-adsorption of desorbed L2 was highly disfavored. Desorption of L2-fluorescein could be followed by the measurement of remaining fluorescein absorbance on QDs over time. As this measurement required the separation of the QDs from the surrounding solution (performed by ultrafiltration), cumulative fluorescein absorbance in solution could be monitored in parallel (FIG. 6, A).

Figure 6:
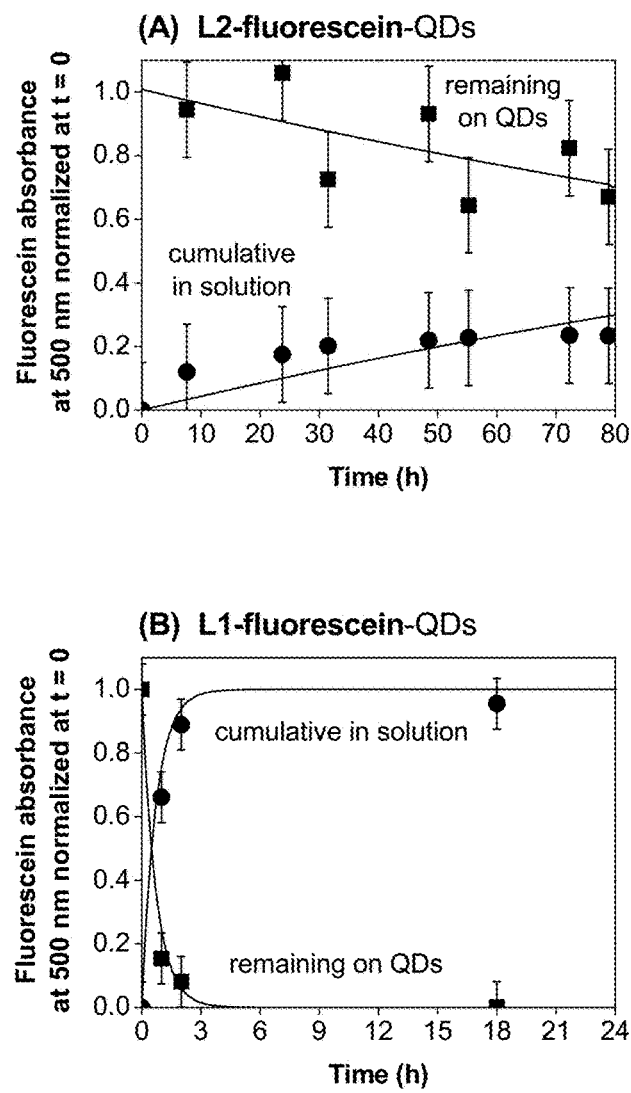
FIG. 6: Monitoring of fluorescein absorbance remaining on L2-fluorescein-QDs (squares) and accumulated in the surrounding solution (circles), during the exchange experiment between competing ligand L1 and adsorbed (capping) ligands L2-fluorescein (A) or L1-fluorescein (B).

The same type of experiment was carried out with L1-fluorescein-QDs versus L1 (FIG. 6, B). In that case, the so-called L1-fluorescein-QDs were QDs covered with a mixture of L1 and a fluorescein-PEG-dithiol bidentate ligand, which were also subjected to a 10,000-fold molar excess of L1. From the modeling of absorption data by an exponential decay, we were able to estimate the corresponding apparent desorption rate constants in the presence of competing L1, namely $k_{off\ L2\text{-}fluorescein} \approx 0.0045$ h$^{-1}$ and $k_{off\ L1\text{-}fluorescein} \approx 1.5$ h$^{-1}$. These results demonstrate undoubtedly the overwhelming stability of L2-type ligands, compared to that of L1-type bidentate ligands.

Stability in an intracellular medium. To conclude the study of L2-QD stability, their behavior in an intracellular environment was examined and compared to L1-QDs. First, HeLa cells were incubated with 1 μM L1- or L2-QD solutions for 6 h. After washing, the fluorescence microscopy image of L2-QD-incubated cells (FIG. 7A) showed no significant difference regarding cellular autofluorescence (FIG. 7C), whereas cells treated with L1-QDs had a slightly higher fluorescence level (FIG. 7B). Even though this level can be considered as low on an absolute scale, this is indicative of a small amount of non-specific adsorption in the case of L1-QDs. As for L2-QDs, they do not present any detectable non-specific adsorption on cell membranes, which represents again a worthwhile improvement.

Figure 8:
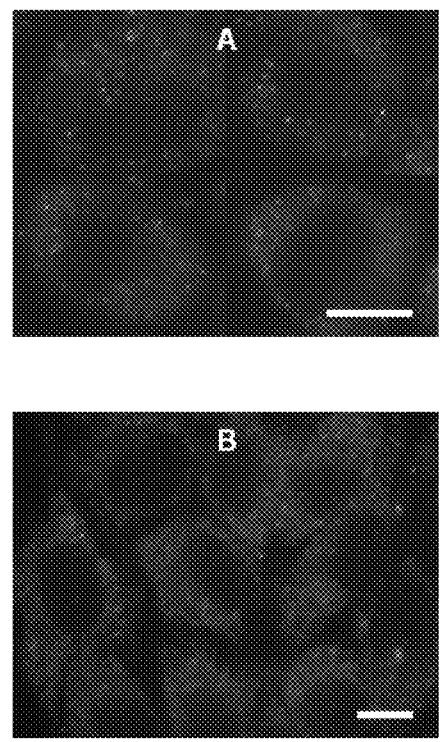
FIG. 8: Fluorescence microscopy images of HeLa cells, 54 h after electroporation (Scale bars 5 µm) and corresponding aggregation quantification. (A) L1-QDs tend to form aggregates (bright spots and heaps); (B) L2-QDs are still individual and move around freely within the cell; (C) Quantification of QDs' aggregation using Sd/M index for different surface chemistries.
Figure 8:
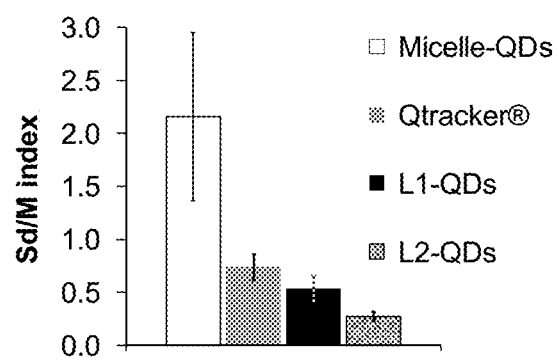

Intracellular stability was checked, in turn, using electroporation as internalization process: via an electric shock, 1 μM solutions of L1- or L2-QDs were incorporated in HeLa cells. The monitoring of QD fluorescence showed that, 54 h after incorporation, L1-QDs begin to aggregate (bright spots, FIG. 8A), while L2-QDs remain individualized, mobile and well distributed throughout cell cytoplasm (FIG. 8B). Quantification of QD aggregation was realized using a method developed in our lab. This method consists in estimating the Standard deviation of pixel fluorescence intensities normalized by their Mean (average) value over the whole cytoplasm (Sd/M index). Briefly, highly dispersed QDs yield uniform cytoplasm labeling and low Sd/M, while bright aggregates spots yield high Sd/M. This index makes a clear difference in favor of L2-QDs, not only compared to L1-QDs, but also to other QDs with various surface chemistries, including QDs encapsulated into poly(ethylene glycol)-phospholipid micelles (Micelle-QDs) and Qtracker®, commercial QDs encapsulated into an amphiphilic copolymer (FIG. 8C). L2-QD stability properties over time are thus definitely confirmed and meet all the relevant conditions for an application in long-term bioimaging.

Towards biotargeting. The possibility of L2-QD functionalization has already been demonstrated by the incorporation of a fluorescent dye in a L2-type polymer before the ligand exchange. To further develop the opportunities for functionalization and tend to biotargeting, we designed and synthesized terpolymer L2-PEG-NH$_2$ bearing a more reachable amine reactive group (longer spacer arm) than in terpolymer L2-NH$_2$ (Scheme 4). The synthesis of the amine-containing monomer D was achieved using a previously described protocol.

Scheme 4. Synthesis of terpolymer L2-PEG-NH₂.

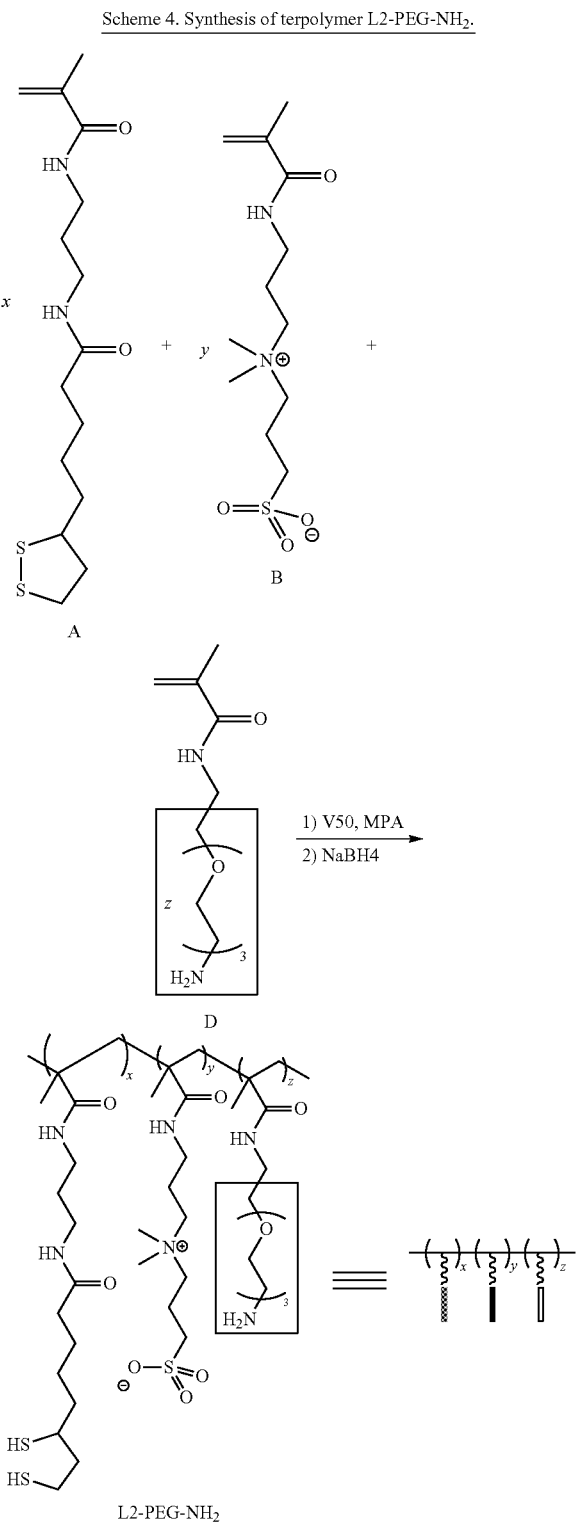

L2-PEG-NH₂

Figure 9:
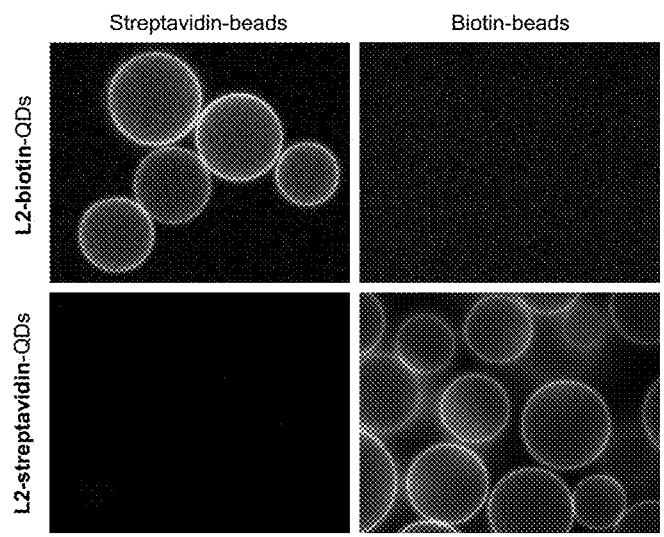
FIG. 9: Specificity of bioconjugated QDs. L2-biotin-QDs specifically bind to streptavidin-beads, while L2-streptavidin-QDs specifically bind to biotin-beads.

The experiment of specific binding relied on the strong non-covalent affinity ($K_a \approx 10^{14}$ L·mol$^{-1}$) between biotin (a small biomolecule) and streptavidin (a 60 kDa protein). After ligand exchange, L2-PEG-NH₂-capped QDs were bioconjugated, via their amine function, with either biotin or streptavidin, using respectively a classical peptidic coupling based on the reagents DCC (dicyclohexylcarbodiimide) and NHS (N-hydroxysuccinimide), or a thiol/maleimide reaction. Bioconjugated QDs, when reacted with either biotin- or streptavidin-functionalized agarose beads, bound specifically to the beads bearing the complementary biomolecule. No non-specific binding could be pointed out (FIG. 9).

Conclusion

Whatever the extreme conditions opposed to our new polymeric ligand (pH, salinity, dilution or adsorption competition), the different experiments reported herein confirmed the outclassing stability of multidentate polyzwitterion L2 at the surface of CdSe/CdS/ZnS QDs, compared to bidentate monozwitterion L1. Moreover, this work led us—for the first time to our knowledge—to display some quantitative information about ligand desorption rates, and to better argue about the improved ligand anchoring the poly (dithiol)s are responsible for, with respect to single dithiol. Finally, L2 excellent properties resulted also in an increased colloidal and intracellular stability of the corresponding L2-coated quantum dots, making this polymer a remarkable ligand for long-term live-cell imaging experiments based on fluorescent nanocrystals.

Additional Results

Materials and Instrumentation

Streptavidin was purchased from Biospa; APMA.HCl (N-(3-aminopropyl)methacrylamide hydrochloride) was purchased from Tebu-bio; SPP (3-sulfopropyldimethyl-3-methacrylamidopropylammonium inner salt; 3-[3-methacrylamidopropyl-(dimethyl)ammonio]propane-1-sulfonate), from Raschig GmbH (Ralu®Mer SPP); sulfo-1c-SPDP (sulfosuccinimidyl 6-(3'-[2-pyridyldithio]-propionamido)hexanoate), sulfo-SMCC (sulfosuccinimidyl-4-(N-maleimidomethyl)cyclohexane-1-carboxylate) and DTT (dithiothreitol), from Pierce; all other chemicals used in this study (including functionalized agarose beads) were purchased from Sigma-Aldrich. All of these purchased chemicals were used without further purification unless otherwise specified. Dry THF was obtained from distillation on sodium/benzophenone ketyl. Chromatography on silica was carried out on Kieselgel 60 (230-240 mesh, Merck) and analytical TLC was performed on Merck precoated silica gel (60 $F_{254}$); chemicals were visualized by heating with a solution of 5-7% phosphomolybdic acid in ethanol. $^1$H NMR spectrum was recorded on a Bruker Avance DPX 400 spectrometer at 400.13 MHz. Chemical shifts (δ) are expressed in ppm and coupling constant (J) in hertz. Absorption measurements were carried out with a Cary 5E UV-vis-NIR spectrophotometer (Varian). Fluorescence measurements were acquired using a Fluoromax-3® fluorimeter (Jobin Yvon, Horiba). Dynamic light scattering measurements (DLS) were performed on a CGS-3 goniometer system equipped with a HeNe laser illumination at 633 nm (Malvern) and an ALV 5000/EPP correlator (ALV).

Polymeric ligands Syntheses

Synthesis of monomer A (5-(1,2-dithiolan-3-yl)-N-(3-methacrylamidopropyl)-pentanamide, Scheme 5)

Scheme 5. Synthesis of monomer A.

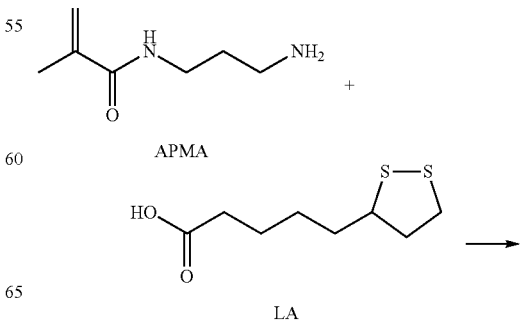

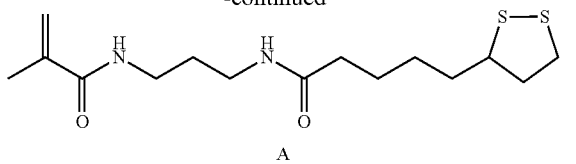

A

To a suspension of APMA.HCl (2 g, 11.2 mmol) in dichloromethane (20 mL) was added triethylamine (2.5 mL, 17.9 mmol). Methanol (2 mL) was introduced to obtain complete solubilization. A solution of LA (2.76 g, 13.4 mmol) in dichloromethane (5 mL) was then added, followed by NHS (1.58 g, 13.8 mmol) in one portion. The reaction mixture was cooled down to 0° C. with an ice bath and a solution of DCC (dicyclohexyl carbodiimide) (3.00 g, 14.4 mmol) in dichloromethane (10 mL) was injected dropwise. The medium was warmed up to room temperature and further stirred overnight. A pale yellow solution containing a white precipitate was obtained. The solution was washed by a 0.1 M aqueous HCl solution (2×50 mL), deionized water (1×50 mL) and a 0.2 M aqueous NaOH solution (2×50 mL). The organic phase was separated, dried over $MgSO_4$, filtrated and concentrated under reduced pressure. The crude residue was purified by chromatography on silica (eluent: hexane/ethyl acetate 1/4, then hexane/acetone 1/1) to give A (2.88 g, 8.71 mmol, 78%) as a pale yellow solid. $R_f$=0.37 (hexane/acetone 1/1); $^1$H NMR ($CDCl_3$, 400 MHz): δ 7.03 (sl, 1H); 6.87 (sl, 1H); 5.72 (s, 1H); 5.29 (s, 1H); 3.53-3.39 (m, 1H); 3.29-3.20 (m, 4H); 3.14-3.01 (m, 2H); 2.43-2.35 (m, 1H); 2.18 (t, J=8.0 Hz, 2H); 1.92 (s, 3H); 1.88-1.80 (m, 1H); 1.68-1.55 (m, 6H); 1.48-1.33 (m, 2H).

Synthesis of polymer b-L2 (poly(5-(1,2-dithiolan-3-yl)-N-(3-methacryl-amidopropyl)pentanamide-co-3-[(3-methacrylamidopropyl)dimethylammonio]-propane-1-sulfonate), Scheme 6)

Scheme 6. Synthesis of polymer b-L2.

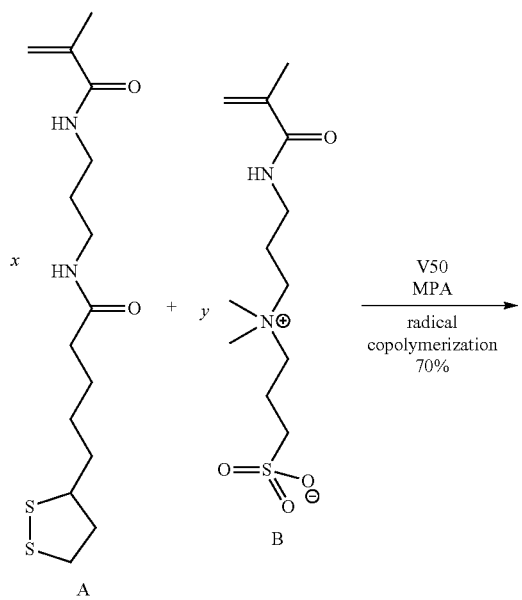

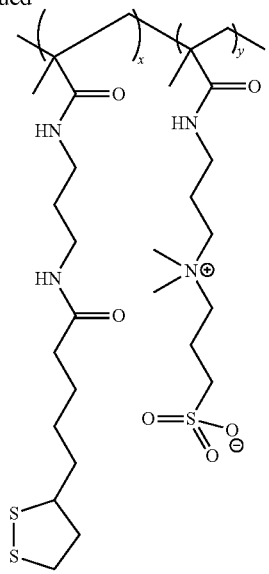

b-L2

To a solution of B (SPP, 1.17 g, 4 mmol, 4 equiv.) in deionized water (20 mL) was added a solution of A (331 mg, 1 mmol, 1 equiv.) in THF (20 mL). A solution of V50 (2,2'-azobis(2-amidinopropane) hydrochloride) (130 mg, 0.5 mmol, 0.5 equiv.) in deionized water (2 mL) was further added in one portion. The pale yellow mixture was stirred and degassed by argon bubbling for 40 min. MPA (42 µL, 0.5 mmol, 0.5 equiv.) was injected into the reaction medium, which was stirred overnight at 60° C. under argon atmosphere. THF was evaporated under reduced pressure; the residual solution was extracted with 20 mL of dichloromethane and the aqueous phase was separated. A 9-fold excess of ethanol was poured into the latter phase to precipitate the polymer, which was separated by centrifugation (50-mL centrifuge tubes, 2,800 g, 10 min) and further dried overnight under vacuum in the presence of $P_2O_5$ as a desiccant. The polymer was obtained as an off-white solid (1.05 g, 70%).

Synthesis of Polymer b-L3. b-L3 was synthesized in the same manner as b-L2, with an A/B molar ratio equal to 10/90 (A: 166 mg, 0.5 mmol; B: 1.28 g, 4.4 mmol; V50: 130 mg, 0.5 mmol; MPA: 42 µL, 0.5 mmol).

Ellman's Dosage (Scheme 7)

Scheme 7. Principle of Ellman's dosage.

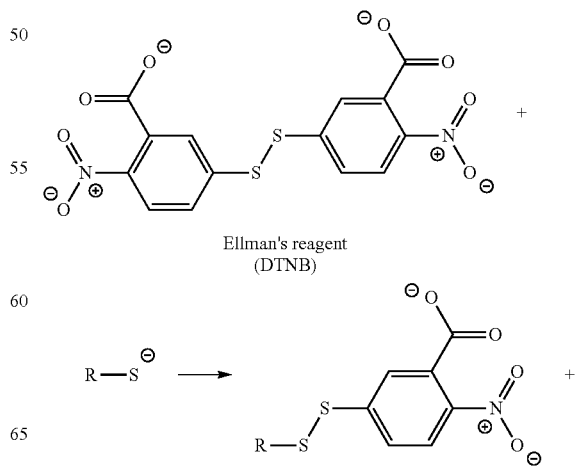

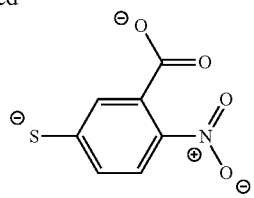

Colored product
$\varepsilon = 14,150 M^{-1}.cm^{-1}$ at
412 nm (7.6 < pH < 8.6)

Dithiol groups of the different polymers were quantified using DHLA (dihydrolipoic acid) as a standard.

A sodium phosphate buffer solution (0.1 M, pH=8) was prepared by dissolving sodium hydrogen phosphate (3.3 g, 23.3 mmol), sodium dihydrogen phosphate (0.2 g, 1.7 mmol) and EDTA (93 mg, 0.3 mmol) in water (250 mL).

Lipoic acid (31 mg, 0.15 mmol) was dissolved in the sodium phosphate solution (5 mL) and the solution was cooled down to 0° C. (ice bath). NaBH₄ (60 mg, 1.6 mmol, 10 equiv.) was added and the mixture was stirred at 0° C. for 30 min. Sulfuric acid (1.5 M, 3 mL) was added and the final volume was adjusted to 50 mL, using the sodium phosphate buffer solution (42 mL), to give a 3-mM solution of DHLA called thereafter "Standard DHLA solution". A set of DHLA standards from 0 to 0.5 mM was prepared from this solution and from the sodium phosphate buffer (see Table 1).

Unknown samples were prepared by dissolving L2 (100 mg) or L3 (200 mg) in sodium phosphate buffer (5 mL). The solutions were cooled down to 0° C., NaBH₄ was added (30 mg) and the mixtures were stirred at 0° C. for 30 min. Sulfuric acid was added to each solution (1.5 M, 1.5 mL), then sodium phosphate buffer (3.5 mL). 2 mL of these solutions were diluted to a final volume of 10 mL to obtain the unknown sample solutions.

Ellman's reagent solution was prepared by dissolving DTNB (5,5'-dithio-bis-(2-nitrobenzoic acid)) (4 mg) in sodium phosphate buffer (1 mL). A set of test tubes was prepared, each containing Ellman's reagent solution (50 μL) and sodium phosphate buffer (2.5 mL).

Each DHLA standard or unknown sample (250 μL) was added to separate test tubes.

Figure 10:
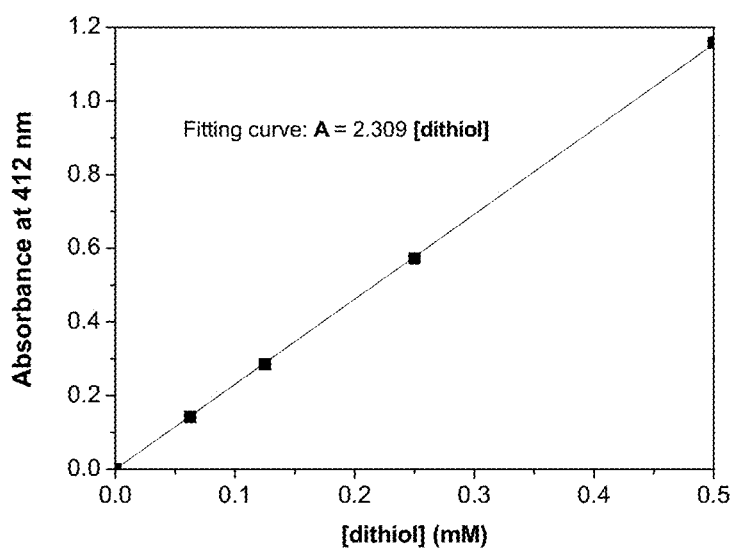
FIG. 10: Ellman's dosage standard curve.

Solutions were mixed, incubated at room temperature for 15 min, and their absorbance at 412 nm was measured. DHLA standards were used to generate a standard curve (FIG. 10) that allowed the determination of unknown concentrations. Results are summarized in Table 1.

Estimation of the real A/B ratio in polymers L2 and L3:

Average number of monomer A/polymeric chain:

$$\langle N_A \rangle = \frac{[\text{dithiol}]_{exp}}{[\text{polymer}]_{sample}}$$

Average number of monomers/polymeric chain:

$$\langle N_A + N_B \rangle \approx \frac{M_n(\text{polymer})}{M_A} (M_A \approx M_B \approx 300 \text{ g.mol}^{-1}) \Rightarrow$$

$$\begin{cases} A/B \approx 7/93 \text{ in } L2 \\ A/B \approx 2/98 \text{ in } L3 \end{cases}$$

CdSe/CdS/ZnS QDs Synthesis 600-nm-emitting CdSe/CdS/ZnS QDs were synthesized using slight modifications of previously published procedures. CdSe cores were synthesized by reaction of trioctylphosphine selenide and cadmium oleate in octadecene, oleylamine and trioctylphosphine oxide. Three monolayers of CdS shell, followed by two monolayers of ZnS, were grown using cadmium oleate, zinc oleate and sulfur diluted in octadecene following the SILAR (Successive Ionic Layer Adsorption and Reaction) procedure.

Figure 11:
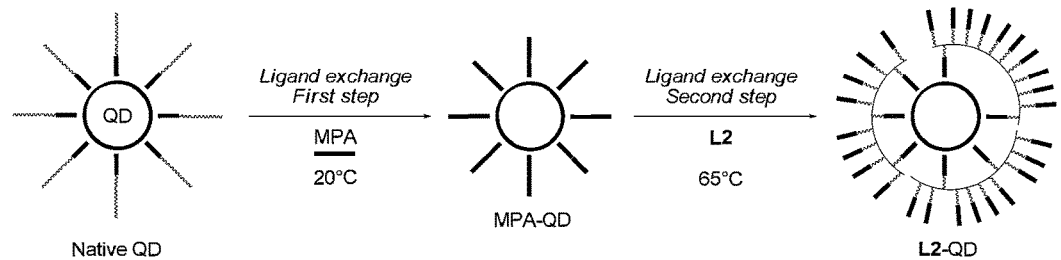
FIG. 11: Ligand exchange L2/QDs.

Ligand Exchange L2/QDs: Standard Procedure (Scheme 8 and FIG. 11)

Scheme 8. Ligand exchange L2/QDs.

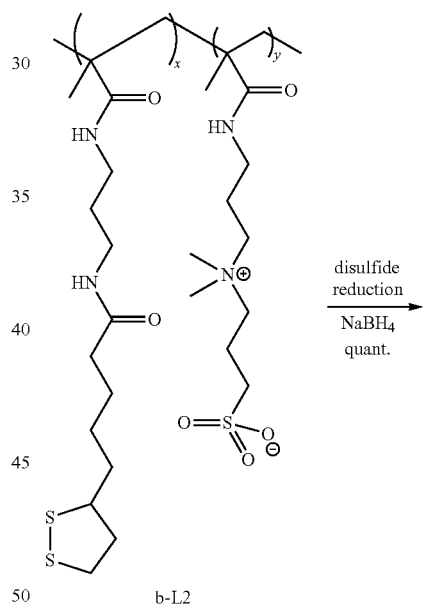

b-L2

TABLE 1

| Ellman's dosage: standard curve generation and determination of unknown sample concentrations. | | | | | |
|---|---|---|---|---|---|
| Sample | $V_{sodium\ phosphate\ buffer}$ | $V_{Standard\ DHLA\ sol.}$ (mL) | [dithiol] (mM) | Absorbance at 412 nm | [dithiol]$_{exp}$ (mM) |
| Standard 1 | 4 | 0 | 0 | 0.000 | |
| Standard 2 | 3.917 | 0.083 | 0.0625 | 0.142 | |
| Standard 3 | 3.833 | 0.167 | 0.125 | 0.285 | |
| Standard 4 | 3.667 | 0.333 | 0.25 | 0.572 | |
| Standard 5 | 3.333 | 0.667 | 0.5 | 1.158 | |
| L2 | | | | 1.045 | 0.453 |
| L3 | | | | 0.693 | 0.300 |

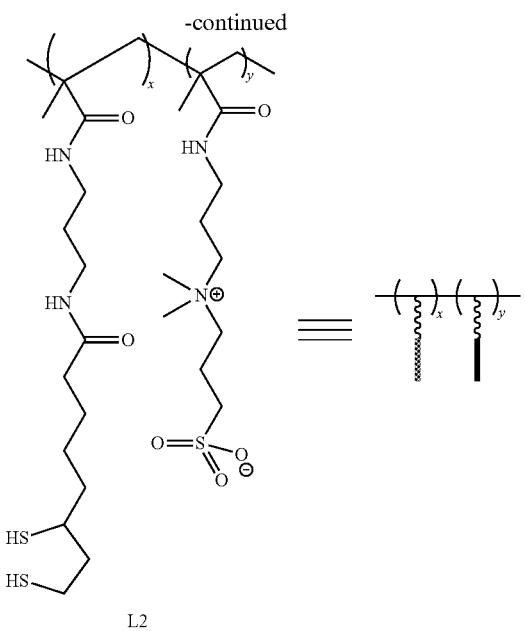

L2

CdSe/CdS/ZnS core/shell QDs in hexane (4 nmol) were precipitated with ethanol and centrifuged (16,000 g, 10 min). The supernatant was removed, the QDs were redispersed in hexane (0.2 mL) and the procedure was repeated once. The QDs were then taken up in chloroform (1 mL). MPA (100 µL, 1.1 mmol) was dissolved in a freshly prepared solution of TMAOH.5H$_2$O (400 mg, 2.2 mmol) in chloroform (2 mL), using a sonicating bath. 1 mL of the basic organic phase was added to the QD colloidal dispersion. The mixture was stirred, then left at room temperature. After 15-30 min typically, MPA-QDs aggregated. The suspension was centrifuged to remove the basic organic supernatant (16,000 g, 5 min) and the nanoparticles were washed twice with chloroform (brief stirring and centrifugation at 16,000 g, 5 min). MPA-QDs were taken up in a 10-mM sodium tetraborate buffer (2 mL, pH=9).

A solution of b-L2 (40 mg) in deionized water (2 mL) was cooled down to 0° C. with an ice bath and NaBH$_4$ (10 mg) was added in one portion. The solution was warmed up slowly to room temperature and stirred for 30 min. The aqueous solution of MPA-QDs was added (2 mL) and the mixture was stirred vigorously at room temperature. After 30 min, the vial containing the aqueous mixture was sealed and stored without stirring at 65° C. overnight to complete cap exchange. The L2-QD aqueous solution was cooled down to room temperature and excess free solubilized ligands and reagents were removed by two rounds of membrane ultrafiltration at 16,000 g using a Sartorius Vivaspin® 500 µL disposable filter (cutoff 30 kDa) in 20 mM aqueous NaCl.

L2-QDs were purified by ultracentrifugation at 268,000 g for 25 min in a 10%-40% sucrose gradient in 20 mM aqueous NaCl. The QD band was collected, residual sucrose was removed by four rounds of ultrafiltration (Vivaspin® 500 µL, cutoff 30 kDa, 16,000 g, 10 min) and L2-QDs were further washed by five rounds of ultrafiltration with a 20 mM NaCl aqueous solution (Vivaspin® 500 µL, cutoff 30 kDa, 16,000 g, 10 min). L2-QDs were finally taken up in 20 mM aqueous NaCl.

Stability Vs pH and Salinity

L2-QDs (12 µL, 16 µM in 20 mM aqueous NaCl) were added to solutions of different pH prepared from HCl or NaOH solutions (300 µL, pH from 1 to 13) containing NaCl (50 mg), or to a saturated aqueous solution of NaCl. L2-QDs colloidal solutions were kept at 4° C. over months and stability (i. e. possible aggregation) was controlled by centrifugation (16,000 g, 5 min).

Stability Vs Dilution (FIG. 2)

The concentrations of the different QD solutions in 20 mM aqueous NaCl were determined by the measurement of their absorbance at 350 nm and the corresponding samples were diluted to 0.3 µM by addition of a 20 mM aqueous NaCl solution. The volume of each sample was in the range of 1 mL. Before each measurement, diluted QD samples were centrifuged at 16,000 g for 5 min. Aggregated QDs fell down at the bottom of the centrifuge tube and the absorbance at 350 nm of the supernatant was then measured. This solution was eventually recovered and left at room temperature until next measurement.

QD samples diluted in a 1 M aqueous NaCl solution were washed beforehand by three rounds of ultrafiltration with a 1 M NaCl aqueous solution (Vivaspin® 500 µL, cutoff 30 kDa, 16,000 g, 10 min).

Ligand Competition Experiments

Competition L2 Fluorescein vs L1

Synthesis of b-L1. See the supporting information in a previous publication from our lab (Scheme 9)

Scheme 9. Synthesis of precursor b-L1.

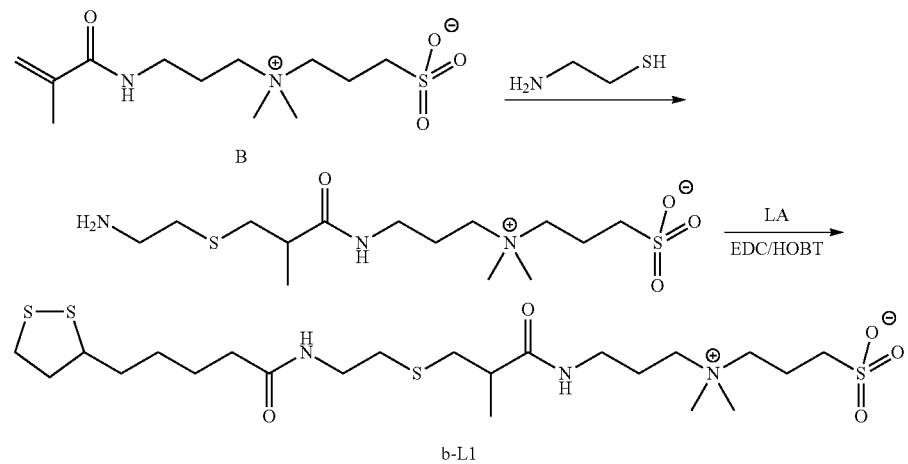

b-L1

Synthesis of Polymer b-L2-Fluorescein

Synthesis of Fluorescein-NHS (Scheme 10)

5(6)-carboxyfluorescein (200 mg, 0.53 mmol, 1 equiv.) was dissolved in DMF (2 mL). NHS (61 mg, 0.53 mmol, 1 equiv.) was added in one portion, then a solution of DCC (110 mg, 0.53 mmol, 1 equiv.) in DMF (0.4 mL), in one portion. The reaction mixture was protected from light and stirred overnight at room temperature. A white precipitate formed, which was filtered and the filtrate was diluted with DMF to obtain a final volume of 5 mL. The reaction was supposed to be quantitative and the solution was stored in the dark at 4° C. until use.

degassed by argon bubbling for 40 min. MPA (42 µL, 0.5 mmol, 1 equiv.) was injected into the reaction medium, which was stirred overnight at 60° C. under argon atmosphere. THF was evaporated under reduced pressure; the residual solution was extracted with 20 mL of dichloromethane and the aqueous phase was separated. A 9-fold excess of ethanol was poured into the latter phase to precipitate the polymer, which was separated by centrifugation (2,800 g, 10 min) and further dried overnight under vacuum in the presence of $P_2O_5$ as a desiccant. The polymer was obtained as an off-white solid (0.69 g, 48%).

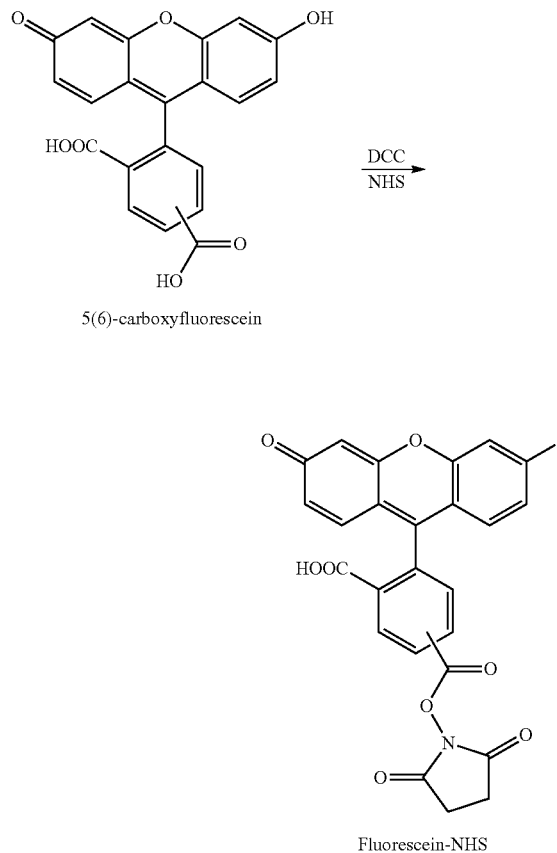

Scheme 10. Synthesis of fluorescein-NHS.

Scheme 11. Synthesis of precursor b-L2-fluorescein.

Synthesis of polymer b-L2-NH$_2$ (poly(N-(3-aminopropyl) methacrylamide-co-5-(1,2-dithiolan-3-yl)-N-(3-methacrylamidopropyl)pentanamide-co-3-[N,N,N-(3-methacrylamidopropyl)-dimethyl-ammonio]propane-1-sulfonate, Scheme 11)

APMA.HCl (89 mg, 0.5 mmol, 1 equiv.), then triethylamine (140 µL, 1 mmol, 2 equiv.) and B (1.03 g, 3.5 mmol, 7 equiv.) were dissolved in deionized water (20 mL). To this solution was added a solution of A (331 mg, 1 mmol, 2 equiv.) in THF (20 mL). A solution of V50 (130 mg, 0.5 mmol, 1 equiv.) in deionized water (2 mL) was further added in one portion. The pale yellow mixture was stirred and

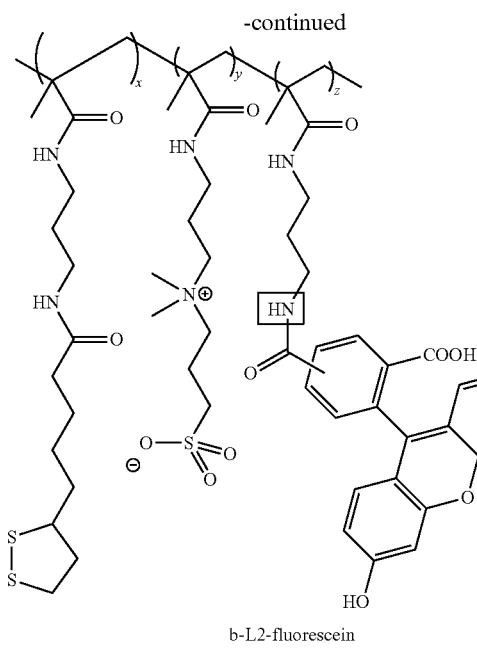

b-L2-fluorescein

Functionalization of b-L2-NH$_2$ by a Fluorescein Dye (Scheme 11)

To a solution of b-L2-NH$_2$ (40 mg) in aqueous NaHCO$_3$ (1.25 mL, 0.2 M, pH=9) was added a solution of fluorescein-NHS in DMF (750 µL, 0.106 M, ≈10 equiv.). The reaction mixture was stirred 2 h at room temperature. The labeled polymer b-L2-fluorescein was purified by several rounds of ultrafiltration (Vivaspin® 500 µL, cutoff 3 kDa, 16,000 g) until the filtrate was not fluorescent anymore. The resulting residue was employed for the ligand exchange without further purification.

Ligand Exchange (Scheme 12)

CdSe/CdS/ZnS core/shell QDs (4 nmol) were exchanged with 20 mg of b-L2-fluorescein, treated beforehand by NaBH$_4$ (10 mg) for 30 min to afford L2-fluorescein, according to the standard two-step process described above for ligand exchange with L2.

Scheme 12. Ligand exchange L2-fluorescein/QDs.

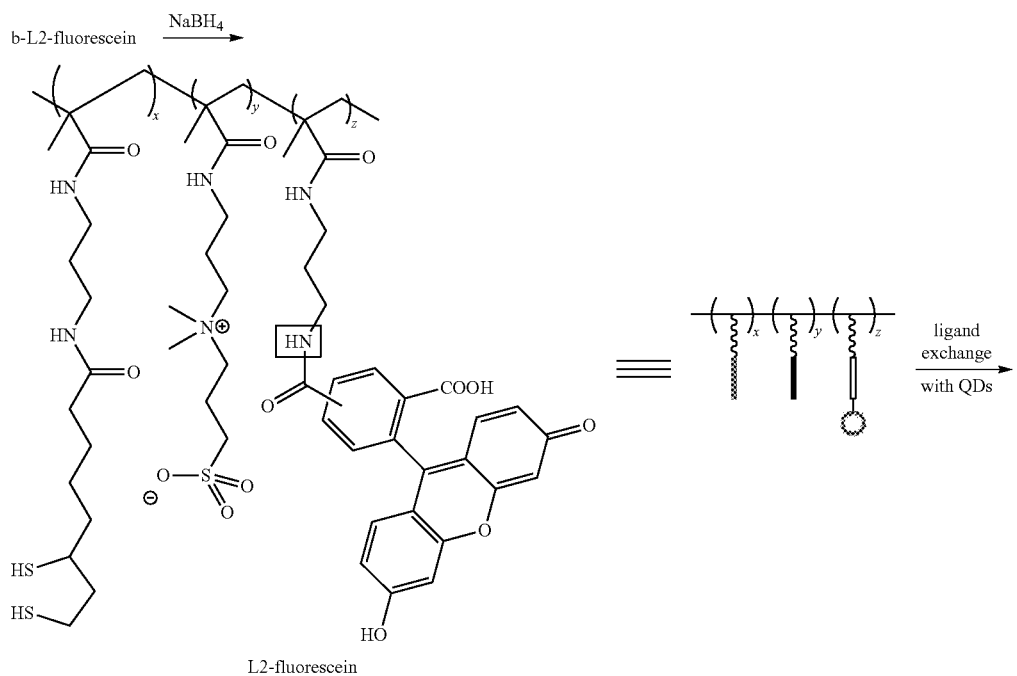

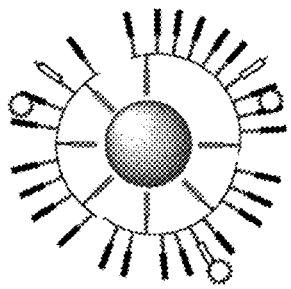

L2-fluorescein-QDs

Number of Functionalizable Amines Per L2-Fluorescein-QDs

Figure 12:
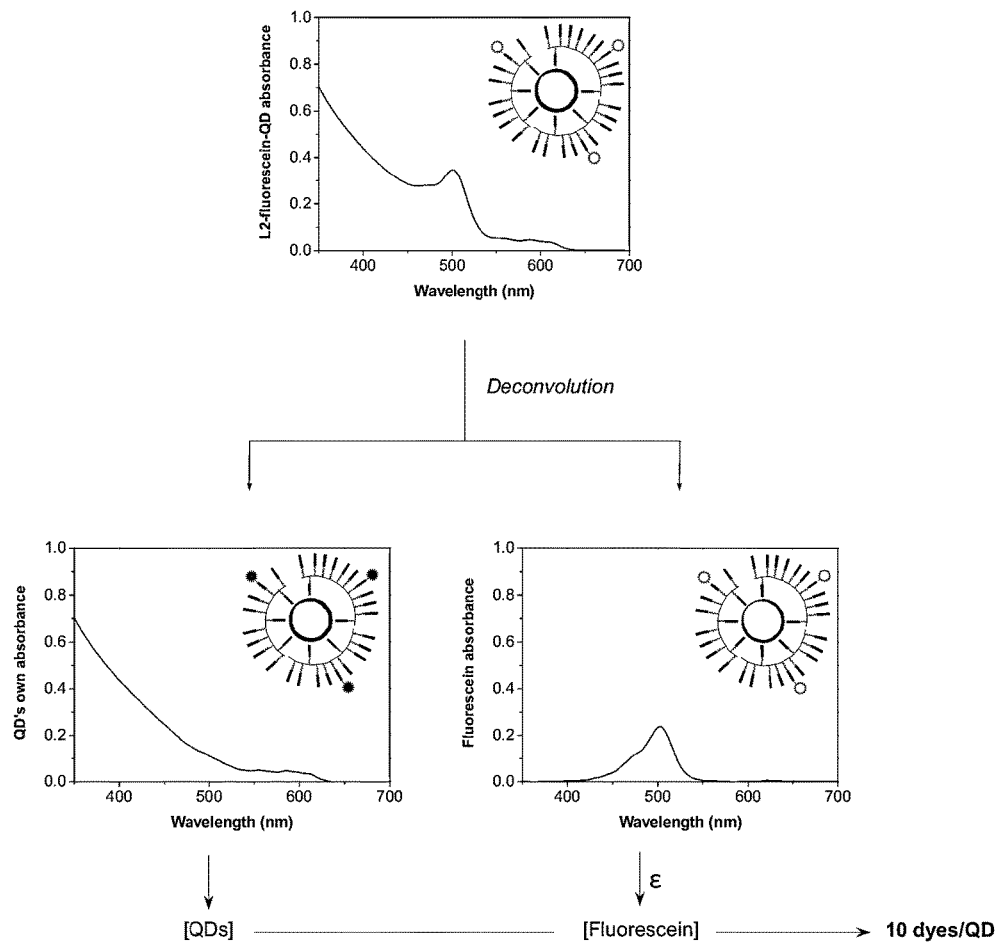
FIG. 12: Determination of the number of functionalizable amines per L2-fluorescein-QDs.

The absorbance at 500 nm of fluorescein-NHS was measured in 0.2 M aqueous NaHCO$_3$ and let us determine the corresponding molar extinction coefficient: $249 = 53,990$ L·mol$^{-1}$·cm$^{-1}$. The absorbance of L2-fluorescein-QDs was measured in the same conditions from 350 to 700 nm. The spectrum was then deconvoluted to separate QD and fluorescein absorbances, as exemplified in FIG. 12. QD absorbance at 350 nm led us to QD concentration; fluorescein absorbance at 500 nm and the corresponding c, to dye concentration. The concentration ratio gave a number of 10 dyes per QD, that is, 10 functionalizable amines per QD.

Ligand Competition and Measurement of L2-Fluorescein Desorption Rate Constant

A solution of b-L1 (100 mg) in 20 mM aqueous NaCl (1 mL) was cooled down to 0° C. with an ice bath and NaBH$_4$ (20 mg) was added in one portion. The solution was warmed up slowly to room temperature and stirred for 30 min. To 120 µL of this L1 solution were added 100 µL of 1 M aqueous HCl, then 480 µL of 1 M aqueous NaHCO$_3$.

L2-fluorescein-QDs (19 µL, 32.3 µM, 0.6 nmol in 0.2 M aqueous NaHCO$_3$, pH=9) were added to the resulting mixture and the absorbance of the solution was measured from 400 nm to 700 nm. This solution, containing L2-fluorescein-QDs and the competing ligand L1, was transferred to a Vivaspin® 500 µL disposable filter (cutoff 30 kDa) and left at room temperature.

Before each next measurement, L2-fluorescein-QDs were separated via ultrafiltration (16,000 g, 10 min) and the surrounding solution was recovered. The absorbance of this surrounding solution was measured and cumulated with previous measurement(s). A freshly prepared 700-µL solution of L1 was added to the QDs and the absorbance of this QD solution was, in turn, measured. Each spectrum of L2-fluorescein-QDs was the deconvoluted to obtain the remaining fluorescein absorbance on QDs.

Figure 13:
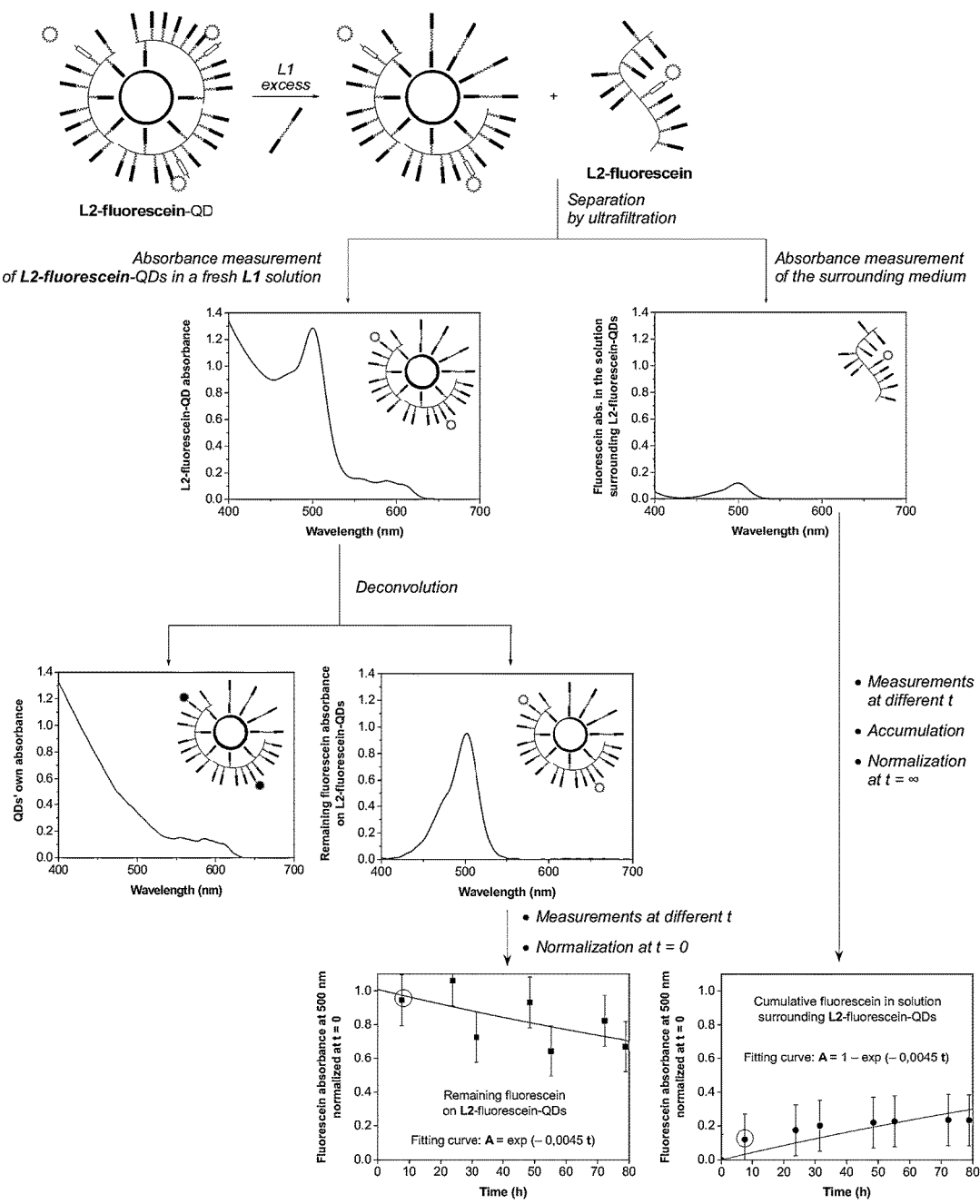
FIG. 13: Determination of L2-fluorescein desorption rate constant.

Measurements were normalized at t=∞ and t=0 respectively, to give the evolution of remaining fluorescein on L2-fluorescein-QDs and the evolution of cumulative fluorescein in solution surrounding L2-fluorescein-QDs, as a function of time. Exponential fittings of experimental data led to the determination L2-fluorescein desorption rate constant, as illustrated in FIG. 13.

Competition L1-Fluorescein vs L1

Synthesis of b-L1. See Scheme 9 and the supporting information in a previous publication from our lab.

Synthesis of b-L1-Fluorescein. b-L1-fluorescein is a LA-PEG-NH$_2$ molecule labeled with fluorescein via fluorescein-NHS (see above for the synthesis of fluorescein-NHS, Scheme 10). LA-PEG-NH$_2$ was synthesized in a five-step process already described and starting from a PEG600 polymer (Scheme 13).

Scheme 13. Synthesis of b-L1-fluorescein and subsequent reduction to L1-fluorescein.

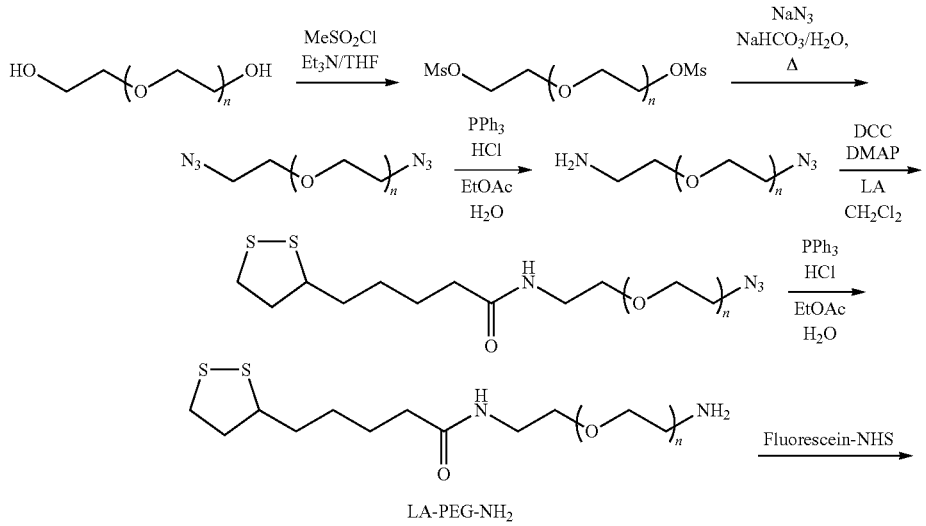

LA-PEG-NH$_2$

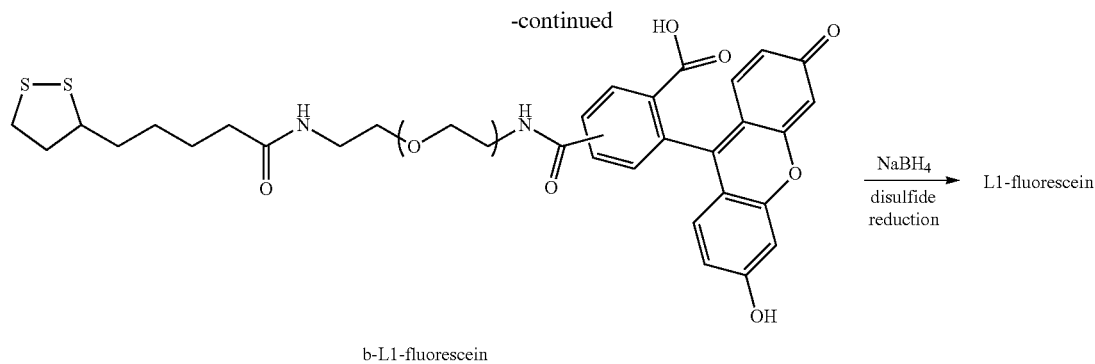

b-L1-fluorescein

Ligand Exchange

CdSe/CdS/ZnS core/shell QDs in hexane (4 nmol) were precipitated with ethanol and centrifuged (16,000 g, 10 min). The supernatant was removed, the QDs were redispersed in hexane (0.2 mL) and the procedure was repeated once. The QDs were then taken up in chloroform (1 mL). b-L1 (100 mg, 1.6 μmol) in deionized water (1 mL) was treated by $NaBH_4$ (20 mg) for 30 min, L1 solution was added to the QDs in chloroform and the biphasic mixture was heated at 65° C. overnight. The aqueous phase was separated and concentrated by ultrafiltration (Vivaspin® 500 μL, cutoff 30 kDa, 16,000 g). L1-QDs were washed with 20 mM aqueous NaCl via three rounds of ultrafiltration (Vivaspin® 500 μL, cutoff 30 kDa, 16,000 g) and taken up in 20 mM aqueous NaCl (200 μL). A solution of b-L1-fluorescein, treated beforehand with $NaBH_4$ to give L1-fluorescein (200 μL, 25 mM in 20 mM aqueous NaCl, ≈10% mol relative to QD-coating-L1), was added to L1-QDs and the mixture was heated at 65° C. overnight. Typical treatment (concentration of the sample, washings with aqueous 20 mM NaCl using ultrafiltration) and purification (ultracentrifugation in a 10%-40% sucrose gradient in 20 mM aqueous NaCl, concentration and washings with 0.2 M aqueous $NaHCO_3$ using ultrafiltration) afforded L1-fluorescein-QDs in 0.2 M aqueous $NaHCO_3$.

Ligand Competition and Measurement of L1-Fluorescein Desorption Rate Constant A solution of competing ligand L1 was prepared as reported above for the measure of L2-fluorescein desorption rate constant. L1-fluorescein-QDs (52 μL, 11.4 μM, 0.6 nmol in 0.2 M aqueous $NaHCO_3$, pH=9) were added to the L1-containing mixture (10 mM) and the absorbance of the solution was measured from 400 nm to 700 nm. This solution, containing L1-fluorescein-QDs and the competing ligand L1, was transferred to a Vivaspin® 500 μL disposable filter (cutoff 30 kDa) and left at room temperature. Before each next measurement, L1-fluorescein-QDs were separated via ultrafiltration (16,000 g, 10 min) and the surrounding solution was recovered. The absorbance of this surrounding solution was measured and cumulated with previous measurement(s).

The time scale of this experiment being far shorter than the determination of L2-fluorescein desorption rate constant, it was not necessary to add systematically a freshly prepared solution of L1 to the QDs before QD absorbance measurement. The initial solution of L1 could be re-used as prepared, except for the last measurement.

Data treatment was performed according to the procedure detailed for L2-fluorescein desorption rate constant in FIG. 13.

Stability in an Intracellular Medium

Cell Culture

HeLa cells were grown in DMEM medium supplemented with 10% FBS and 1% antibiotics.

Non-Specific Adsorption on HeLa Cell Membranes

Figure 7:
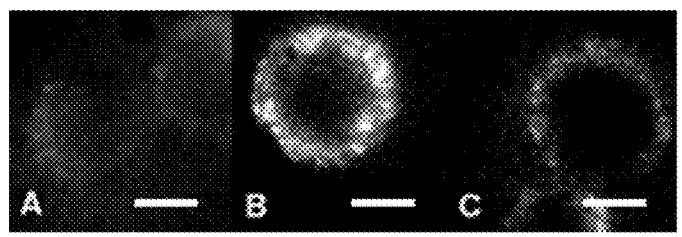
FIG. 7: Fluorescence microscopy images of HeLa cells, after incubating with L2-QDs (A) or L1-QDs (B) and washing, compared to cellular autofluorescence (C). Scale bars 5 µm.

Cells were incubated at 37° C. with L1- or L2-QDs diluted to 1 μM in Opti-MEM® for 10 min (FIG. 7). Cells were then rinsed five times (centrifugation) and imaged. The non-specific adsorption on cell membranes of L2-QDs was comparable with L1-QDs and is almost not detectable.

All images were acquired with the same parameters, using a widefield epifluorescence microscope (IX71 Olympus), a 60×1.2 NA water objective and an EM CCD camera (cascade 512B Roper). Excitation and collection of fluorescence of QDs were performed with 425/60 nm and 605/40 band pass filters.

Electroporation of HeLa Cells

L1- or L2-QDs were diluted in DMEM to 1 μM in a final volume of 100 μL and mixed to 50×10$^4$ cells in suspension in a 2 mm electroporation cuvette. The cuvette was subjected to 0.15 kV for a 28 ms pulse using a Gene Pulser (Biorad) electroporator. Cells were rinsed 3 times, and deposed on LabTek in DMEM/F12 medium supplemented with 10% FBS, 1% antibiotics and 1% HEPES. Cells were imaged after 54 h at 37° C., 5% $CO_2$.

All images were acquired with a widefield epifluorescence microscope (IX71 Olympus) using a 60×1.2 NA water objective, Chroma filters and an EM CCD camera (cascade 512B Roper).

Aggregation quantifications with micelle-QDs and Qtracker®, showed for comparison in FIG. 8C, were performed in the same conditions as those described above. Micelle-QDs were prepared from the encapsulation of CdSe/CdS/ZnS QDs in 100% 1,2-dipalmitoyl-sn-glycero-3-phosphoethanolamine-N-[methoxypoly(ethylene glycol)-2000] carboxamide (Nova) micelles (Scheme 14). Qtracker® 655 non-targeted QDs were purchased from Invitrogen.

Scheme 14. Structure of 1,2-dipalmitoyl-sn-glycero-3-phosphoethanolamine-N-[methoxypoly(ethylene glycol)-2000]carboxamide.

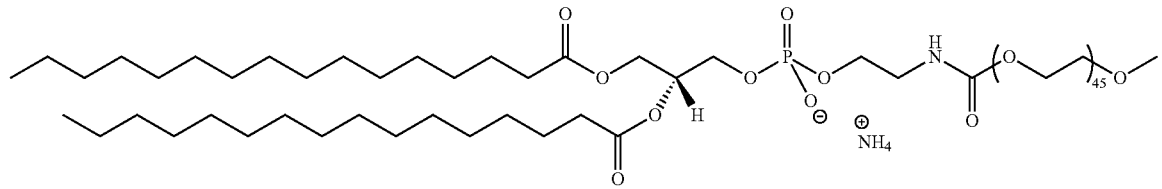

Towards Biotargeting

Monomer D synthesis. Monomer D was synthesized from tetra(ethylene glycol), according to a four-step process (Scheme 15), adapted from a protocol initially developed with a PEG600 as starting material.

Scheme 15. Synthesis of monomer D.

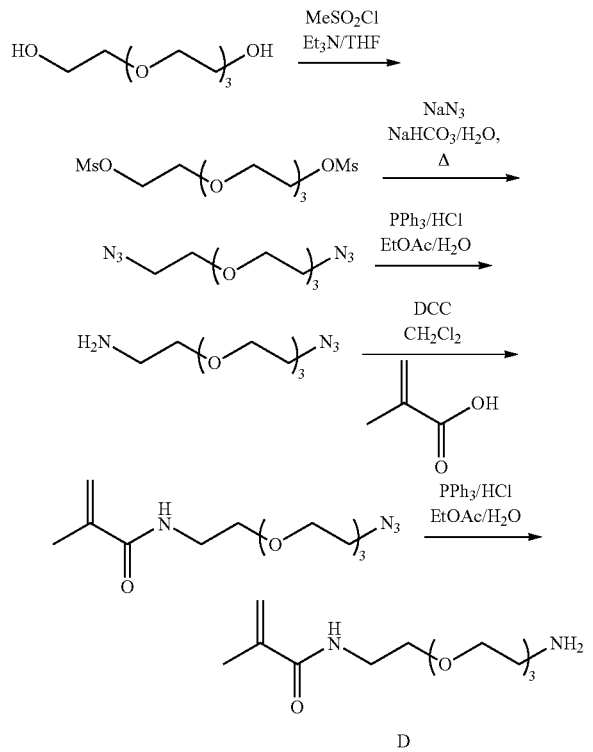

b-L2-PEG-NH$_2$ synthesis. The synthesis of this terpolymer (Scheme 16) was carried out according to the procedure described for the synthesis of L2-NH$_2$ (see the Competition experiment section).

Scheme 16. Synthesis of polymer b- L2-NH2.

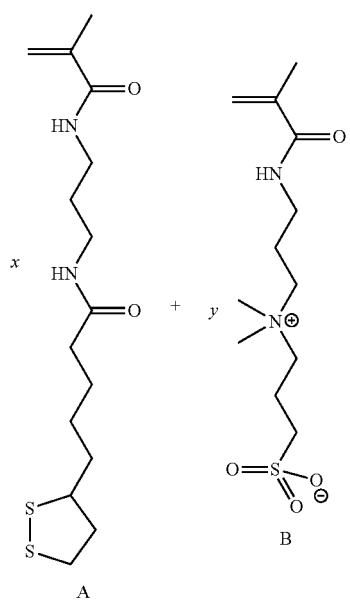

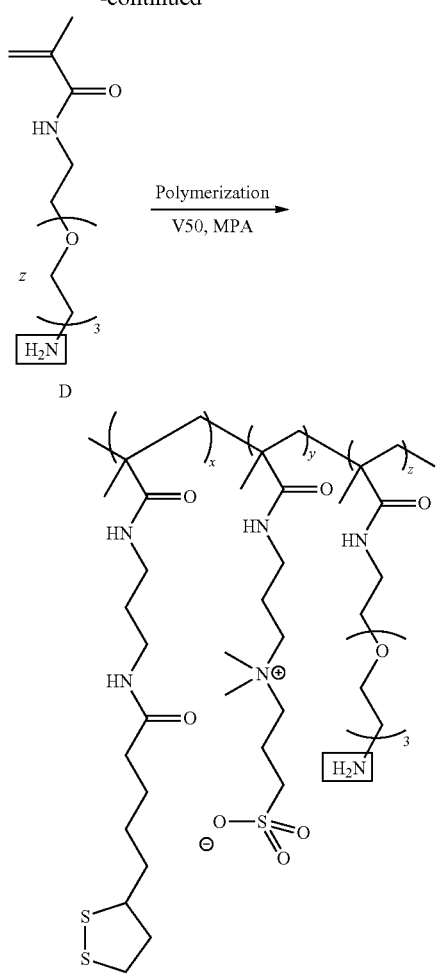

b-L2-PEG-NH$_2$

Ligand exchange L2-PEG-NH$_2$/QDs. Ligand exchange was performed according to the standard procedure indicated for L2, with 20 mg of b-L2-PEG-NH$_2$ treated by 10 mg of NaBH$_4$, for 4 nmol of CdSe/CdS/ZnS QDs (FIG. 14).

L2-PEG-NH$_2$-QD/biotin coupling (FIG. 14). 0.1 mmol of biotin were mixed with equimolar amounts of DCC and NHS in 10 mL DMF and stirred at room temperature overnight to yield a solution of 10 mM NHS-activated biotin. Then 0.5 nmol of L2-PEG-NH$_2$-QDs were diluted in 400 µL sodium bicarbonate buffer (0.2 M, pH=9), and mixed with 50 nmol of NHS-biotin for 30 min. The QDs were then purified with one round of ultrafiltration on Vivaspin 30 kDa (16,000 g, 10 min), one filtration on a NAP-5 column (GE Healthcare) and one final round of ultrafiltration (Vivaspin 30 kDa, 16,000 g, 10 min).

Figure 14:
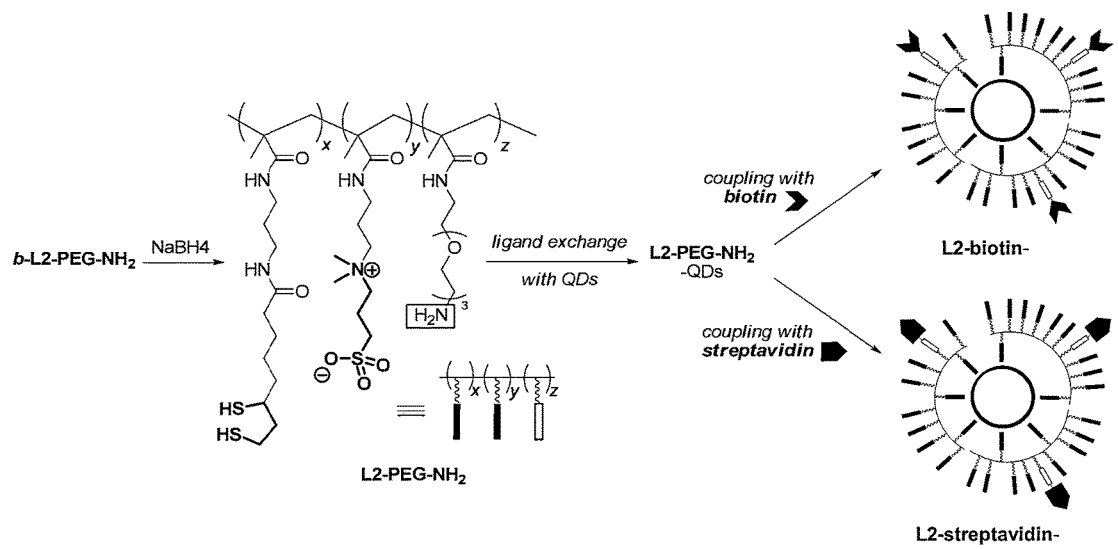
FIG. 14: Ligand exchange L2-PEG-NH$_2$/QDs and bioconjugation with biotin or streptavidin.

L2-PEG-NH$_2$-QD/streptavidin coupling (FIG. 14). Typically, QDs capped with L2-PEG-NH$_2$ (1 nmol) were dispersed in a NaHCO$_3$ buffer (400 µL, 0.2 M, pH=9) and mixed with a sulfo-1c-SPDP solution (30 µL, 10 mg/mL in DMSO) for 15 min. The solution was then concentrated using ultrafiltration (30 kDa MW cutoff, Vivaspin®, Vivascience, 16,000 g, 10 min) and diluted in a NaHCO$_3$ buffer (400 µL, 0.2 M). Then a DTT solution (20 µL, 23 mg/mL in DMSO) was added, and the solution was stirred for 15 min.

The DTT was eliminated using one round of ultrafiltration (16,000 g, 10 min), followed by purification on a NAP-5 column and another round of ultrafiltration (16,000 g, 10 min). The resulting concentrated QD solution was diluted in a HEPES buffer (300 μL, 0.1 M, pH=7).

In another vial, streptavidin (1 mg) diluted in a NaHCO₃ buffer (200 μL, 0.2 M) was mixed with a sulfo-SMCC solution (2.6 μL, 10 mg/mL in DMSO) for 20 min, concentrated with one round of ultrafiltration (30 kDa MW cutoff Vivaspin®, 16,000 g, 10 min) and rediluted with a HEPES buffer (300 μL, 0.1 M).

The resulting freshly prepared QD and streptavidin solutions were mixed together and stirred for 20 min at room temperature. The resulting streptavidin-QD solution was then concentrated using ultrafiltration (16,000 g, 10 min). Excess streptavidin was eliminated using ultracentrifugation on a 10%-40% sucrose gradient (268,000 g, 25 min), and the functionalized streptavidin-QDs were finally reconcentrated using ultrafiltration (16,000 g, 10 min) and redispersed in HEPES buffer.

Figure 15:
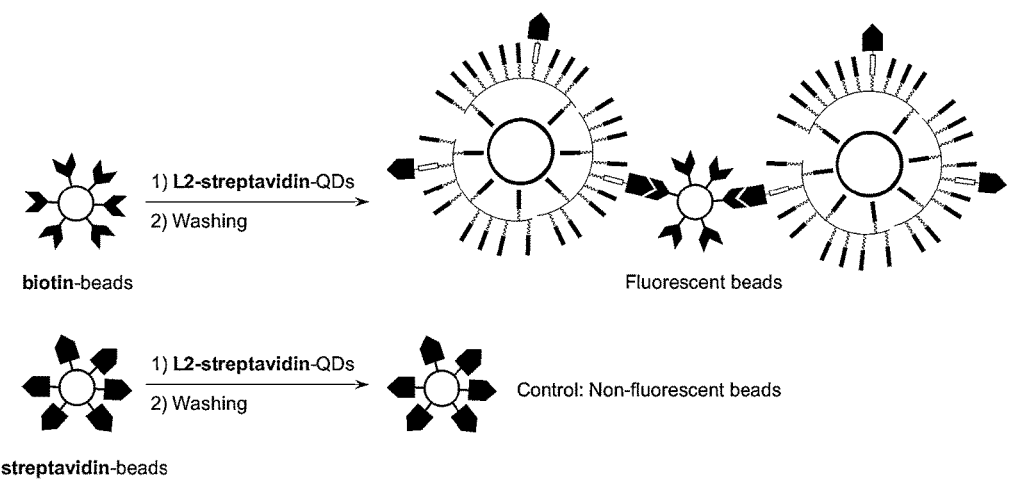
FIG. 15: Control of L2-PEG-NH$_2$-QD bioconjugation with streptavidin (not to scale).

Control of the Bioconjugation with Functionalized Agarose Beads. The efficiency of the conjugation was checked by mixing, during 15 min, 6 pmol of L2-streptavidin-QDs with biotin-functionalized agarose beads. The beads were washed four times in HEPES by mild centrifugation. The control was performed by mixing L2-streptavidin-QDs with streptavidin-functionalized agarose beads. Only the biotin-functionalized beads appeared fluorescent (FIG. 15).

The bioconjugation of biotin to form L2-biotin-QDs was tested in the same way on streptavidin-functionalized agarose beads, with a control on biotin-functionalized agarose beads.

The invention claimed is:

1. A ligand having colloidal stability properties and having the following formula II:

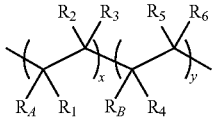

wherein
$R_A$ has the formula $-L_A-M_A$:

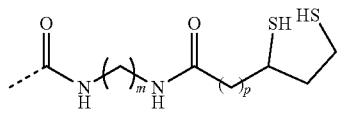

wherein m is an integer ranging from 1 to 5, and p is an integer ranging from 1 to 6;
$R_B$ has the formula $-L_B-M_B$:

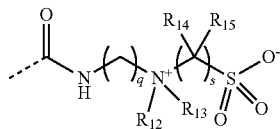

wherein:
q is an integer ranging from 1 to 5,
s is an integer ranging from 1 to 5, and
$R_{12}$, $R_{13}$, $R_{14}$ and $R_{15}$ are each independently H, or a group selected from an alkyl, alkenyl, aryl, hydroxyl, halogen, alkoxy and carboxylate; and
each of x and y is independently a positive integer,
$R_1$, $R_2$, $R_3$, $R_4$, $R_5$, and $R_6$ can be independently H, or a group selected from an alkyl, alkenyl, aryl, hydroxyl, halogen, alkoxy, or carboxylate,
wherein the ligand has a molecular weight from about 1 000 g/mol to about 50 000 g/mol.

2. The ligand according to claim 1, wherein x+y is ranging from 5 to 500.

3. The ligand according to claim 1, being functionalized with at least one molecular probe and/or targeting group.

4. A nanocrystal which is complexed with at least one ligand according to claim 1.

5. The nanocrystal according to claim 4, wherein said nanocrystal is a 0D, 1D, or 2D nanocrystal.

6. The nanocrystal according to claim 4, wherein said nanocrystal is a nanosheet, a nanorod, a nanoplatelet, a nanoplate, a nanoprism, a nanowall, a nanodisk, a nanoparticle, a nanowire, a nanopowder, a nanotube, a nanotetrapod, a nanoribbon, a nanobelt, a nanoneedle, a nanocube, a nanoball, a nanocoil, a nanocone, a nanopiller, a nanoflower, or a quantum dot.

* * * * *